US011111222B2

(12) United States Patent
Holinstat et al.

(10) Patent No.: US 11,111,222 B2
(45) Date of Patent: Sep. 7, 2021

(54) HYDROXYEICOSATRIENOIC ACID COMPOUNDS AND THEIR USE AS THERAPEUTIC AGENTS

(71) Applicants: THE REGENTS OF THE UNIVERSITY OF MICHIGAN, Ann Arbor, MI (US); THE REGENTS OF THE UNIVERSITY OF CALIFORNIA, Oakland, CA (US)

(72) Inventors: Michael Holinstat, Ann Arbor, MI (US); Theodore R. Holman, Santa Cruz, CA (US); Andrew White, Ann Arbor, MI (US)

(73) Assignees: THE REGENTS OF THE UNIVERSITY OF MICHIGAN, Ann Arbor, MI (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/312,721

(22) PCT Filed: Jun. 23, 2017

(86) PCT No.: PCT/US2017/038994
§ 371 (c)(1),
(2) Date: Dec. 21, 2018

(87) PCT Pub. No.: WO2017/223447
PCT Pub. Date: Dec. 28, 2017

(65) Prior Publication Data
US 2019/0161456 A1 May 30, 2019

Related U.S. Application Data

(60) Provisional application No. 62/353,917, filed on Jun. 23, 2016.

(51) Int. Cl.
| C07D 257/04 | (2006.01) |
| C07D 249/04 | (2006.01) |
| C07D 249/08 | (2006.01) |
| C07D 261/12 | (2006.01) |
| A61K 31/202 | (2006.01) |
| A61K 31/4192 | (2006.01) |
| A61K 31/4196 | (2006.01) |
| A61K 31/42 | (2006.01) |
| A61P 7/02 | (2006.01) |
| C07C 59/42 | (2006.01) |
| C07C 305/14 | (2006.01) |
| C07D 233/84 | (2006.01) |
| C07D 249/12 | (2006.01) |
| C07F 9/11 | (2006.01) |

(52) U.S. Cl.
CPC .......... *C07D 257/04* (2013.01); *A61K 31/202* (2013.01); *A61K 31/4192* (2013.01); *A61K 31/4196* (2013.01); *A61K 31/42* (2013.01); *A61P 7/02* (2018.01); *C07C 59/42* (2013.01); *C07C 305/14* (2013.01); *C07D 233/84* (2013.01); *C07D 249/04* (2013.01); *C07D 249/12* (2013.01); *C07F 9/11* (2013.01)

(58) Field of Classification Search
CPC .. C07D 257/04; C07D 249/04; C07D 249/08; C07D 261/12
See application file for complete search history.

(56) References Cited

U.S. PATENT DOCUMENTS

| 6,376,688 B1 | 4/2002 | Ferrante et al. |
| 2003/0108596 A1 | 6/2003 | Sung |
| 2015/0209441 A1 | 7/2015 | Carell |

FOREIGN PATENT DOCUMENTS

| GB | 1156465 A | 6/1969 |
| WO | WO-2001/060778 A2 | 8/2001 |
| WO | WO-2008/079328 A2 | 7/2008 |
| WO | WO-2008/086495 A1 | 7/2008 |
| WO | WO-2015/054662 A1 | 4/2015 |

OTHER PUBLICATIONS

Gosselin, CAS Doc No. 133:130274, entered into STN on Jul. 26, 2000, p. 1-2 (Year: 2000).*
Ahrens and Peter, Humanizing mouse thrombi, *Nat. Biotechnol.*, 26:62-63 (2008).
Armstrong et al., Prostaglandin endoperoxide analogues which are both thromboxane receptor antagonists and prostacyclin mimetics, *Br. J. Pharmac.*, 87:543-551 (1986).
Bunting et al., Arterial walls generate from prostaglandin endoperoxides a substance (prostaglandin X) which relaxes strips of mesenteric and coeliac arteries and inhibits platelet aggregation, *Prostaglandins*, 12:897-913 (1976).
Bunting et al., Formation of prostaglandin endoperoxides and rabbit aorta contracting substance (RCS) by coupling two enzyme systems, *Br J Pharmacol*, 56:344P-345P (1975).
Butt et al., cAMP- and cGMP-dependent Protein Kinase Phosphorylation Sites of the Focal Adhesion Vasodilator-stimulated Phosphoprotein (VASP) in Vitro and in Intact Human Platelets, *J Biol Chem*, 269(20):14590-14517 (1994).
Börsch-Haubold et al., Cytosolic Phospholipase $A_2$ Is Phosphorylated in Collagen- and Thrombin-stimulated Human Platelets Independent of Protein Kinase C and Mitogen-activated Protein Kinase, *The Journal of Biological Chemistry*, 270(43):25885-25892 (1995).

(Continued)

Primary Examiner — Karen Cheng
(74) Attorney, Agent, or Firm — Marshall, Gerstein & Borun LLP

(57) ABSTRACT

12(S)-hydroxyeicosatrienoic acid (12(S)-HETrE) compounds and compositions comprising the same are disclosed. Methods of using the compounds in the prevention and treatment of thrombosis and thrombotic disorders are also disclosed.

20 Claims, 10 Drawing Sheets

(56) References Cited

OTHER PUBLICATIONS

Capodanno et al., Meta-Analyses of Dual Antiplatelet Therapy Following Drug-Eluting Stent Implantation, *J Am Coll Cardiol*, 66(14):1639-1640 (2015).

Chen et al., Addition of clopidogrel to aspirin in 45 852 patients with acute myocardial infarction: randomised placebo-controlled trial, *Lancet*, 366:1607-21 (2005).

De Oliveira Otto et al., Circulating and Dietary Omega-3 and Omega-6 Polyunsaturated Fatty Acids and Incidence of CVD in the Multi-Ethnic Study of Atherosclerosis, *J Am Heart Assoc.*, 2:e000506 (2013).

Diener et al., Aspirin and clopidogrel compared with clopidogrel alone after recent ischaemic stroke or transient ischaemic attack in high-risk patents (MATCH): randomised, double-blind, placebo-controlled trial, *Lancet*, 364:331-37 (2004).

Dyerberg et al., Eicosapentaenoic acid and prevention of thrombosis and atherosclerosis?, *Lancet*, 312(8081):117-119 (1978).

Falardeau et al., Metabolism of 8,11,14-eicosatrienoic acid in human platelets, *Biochim. Biophys. Acta*, 441:193-200 (1976).

Falati et al., Real-time in vivo imaging of platelets, tissue factor and fibrin during arterial thrombus formation in the mouse, *Nat Med*, 8:1175-1181 (2002).

Farrow and Willis, Thrombolytic and anti-thrombotic properties of dihomo-γ-linolenate in vitro, *Br J Pharmacol*, 55:316P-317P (1975).

Gilman, Alfred, Guanine Nucleotide-binding Regulatory Proteins and Dual Control of Adenylate Cyclase, *J. Clin. Invest.*, 73:1-4 (1984).

Gorman et al., Modulation of human platelet adenylate cyclase by prostacyclin (PGX), *Prostaglandins*, 13:377-388 (1977).

Hamberg and Samuelsson, Prostaglandin Endoperoxides. Novel Transformations of Arachidonic Acid in Human Platelets, *Proc. Nat. Acad. Sci. USA*, 71(9):3400-3404 (1974).

Haslam et al., Cyclic Nucleotides in Platelet Function, *Thromb Haemost*, 40:232-240 (1978b).

Haslam et al., Regulation of blood platelet function by cyclic nucleotides, *Adv Cyclic Nucleotide Res*, 9:533-552 (1978a).

Haslam, Roles of cyclic nucleotides in platelet function, *Ciba Found Symp*, 35:121-151 (1975).

Ikei et al., Investigations of human platelet-type 12-lipoxygenase: role of lipoxygenase products in platelet activation, *J Lipid Res*, 53:2546-2559 (2012).

International Preliminary Report on Patentability, Chapter I, for International Application No. PCT/US2017/38994, issued by the International Bureau on behalf of the International Searching Authority, dated Dec. 25, 2018.

International Search Report and Written Opinion of the International Searching Authority, for International Application No. PCT/US17/38994, dated Sep. 29, 2017.

Kernoff et al., Antithrombotic potential of dihomo-gammalinolenic acid in man, *Br Med J*, 2:1441-1444 (1997).

Lands and Samuelsson, Phospholipid precursors of prostaglandins, *Biochim. Biophys. Acta*, 164:426-429 (1968).

Lee et al., Safety and efficacy of targeting platelet proteinase-activated receptors in combination with existing anti-platelet drugs as antithrombotics in mice, *Br J Pharmacol*, 166:2188-2197 (2012).

Levin et al., Differential metabolism of dihomo-γ-linolenic acid and arachidonic acid by cyclo-oxygenase-1 and cyclo-oxygenase-2: implications for cellular synthesis of prostaglandin $E_1$ and prostaglandin $E_2$, *Biochem. J.*, 365:489-496 (2002).

Miller and Gorman, Modulation of platelet cyclic nucleotide content by PGE1 and the prostaglandin endoperoxide PGG2, *J Cyclic Nucleotide Res*, 2(2):79-87 (1976).

Moncada et al., An enzyme isolated from arteries transforms prostaglandin endoperoxides to an unstable substance that inhibits platelet aggregation, *Nature*, 263(5579):663-665 (1976).

National Center for Biotechnology Information. PubChem Database. KEYMETUQXWLIPS-XCHAJGETSA-N, CID=46872402, https://pubchem.ncbi.nlm.nih.gov/compound/46872402 (Create Date: Sep. 20, 2010).

Needleman et al., Manipulation of platelet aggregation by prostaglandins and their fatty acid precursors: pharmacological basis for a therapeutic approach, *Prostaglandins*, 19(1):165-181 (1980).

Noe et al., Regulators of Platelet cAMP Levels: Clinical and Therapeutic Implications, *Curr Med Chem*, 17(26):2897-2905 (2010).

Nyby et al., Platelet Lipoxygenase Inhibitors Attenuate Thrombin- and Thromboxane Mimetic-Induced Calcium Mobilization and Platelet Aggregation, *J. Pharmacol. Exp. Ther.*, 278(2):503-509 (1996).

Palacio et al., Effect of Addition of Clopidogrel to Aspirin on Mortality: Systematic Review of Randomized Trials, *Stroke*, 43(8):2157-2162 (2012).

Reheman et al, Plasma fibronectic depletion enhances platelet aggregation and thrombus formation in mice lacking fibrinogen and von Willebrand factor, *Blood*, 113(8):1809-1817 (2009).

Reheman et al., Vitronectin stabilizes thrombi and vessel occlusion but plays a dual role in platelet aggregation, *J Thromb Haemost*, 3:875-883 (2005).

Riva et al., Iloprost inhibits neutrophil-induced lung injury and neutrophil adherence to endothelial monolayers, *Am J Respir Cell Mol Biol*, 3:301-309 (1990).

Samuelsson, Role of Basic Science in the Development of New Medicines: Examples from the Eicosanoid Field, *J Biol Chem*, 287(13):10070-10080 (2012).

Shattil and Newman, The final steps of integrin activation: the end game, *Blood*, 104(6):1606-1615 (2004).

Shattil et al., The final steps of integrin activation: the end game, *Nat Rev Mol Cell Biol.*, 11(4):288-300 (2010).

Simon et al., Human platelet microRNA-mRNA networks associated with age and gender revealed by integrated plateletomics, *Blood*, 123:e37-e45 (2014).

Smigel et al., Mechanisms of guanine nucleotide-mediated regulation of adenylate cyclase activity, *Advances in Cyclic Nucleotide and Protein Phosphorylation Research*, 17:1-18 (1984).

Srivastava, Metabolism of Arachidonic Acid by Platelets: Utilization of Arachidonic Acid by Human Platelets in Presence of Linoleic and Dihomo-γ-Linolenic Acids, *Z Ernahrungswiss*, 17:248-261 (1978).

Stolla et al., CalDAG-GEFI deficiency protects mice in a novel model of FcγRIIA-mediated thrombosis and thrombocytopenia, *Blood*, 118(4):1113-1120 (2011).

Tateson et al., Effects of prostacyclin (PGX) on cyclic AMP concentrations in human platelets, *Prostaglandins*, 13(3):389-397 (1977).

Thomas et al., Phospholipid-esterified eicosanoids are generated in agonist-activated human platelets and enhance tissue factor-dependent thrombin generation, *J Biol Chem*, 285(10):6891-6903 (2010).

Tourdot et al., The emerging role of oxylipins in thrombosis and diabetes, *Front Pharmacol*, 4:176 (2014).

Turcato and Clapp, Effects of the adenylyl cyclase inhibitor SQ22536 on iloprost-induced vasorelaxation and cyclic AMP elevation in isolated guinea-pig aorta, *Br J Pharmacol*, 126(4):845-847 (1999).

Wada et al., Enzymes and Receptors of Prostaglandin Pathways with Arachidonic Acid-derived Versus Eicosapentaenoic Acid-derived Substrates and Products, *J Biol Chem*, 282(31):22254-22266 (2007).

Wang et al., Plasma fibronectin supports hemostasis and regulated thrombosis, *J Clin Invest*, 124(10):4281-4293 (2014).

Welsh et al., A systems approach to hemostasis: 4. How hemostasis thrombi limit the loss of plasma-borne molecules from the microvasculature, *Blood*, 127(12):1598-1605 (2016).

Willis et al., Dihomo-gamma-linolenate suppresses platelet aggregation when administered in vitro or in vivo, *Prostaglandins*, 9:509-519 (1974).

Yeung and Hollinstat, Who is the real 12-HETrE?, *Prostaglandins Other Lipid Mediat.*, 132:25-30 (2017).

Yeung et al., 12-lipoxygenase activity plays an important role in PAR4 and GPVI-mediated platelet reactivity, *Thromb Haemost.*, 110(3):569-581 (2013).

Yeung et al., Platelet 12-LOX is essential for FCγRIIa-mediated platelet activation, *Blood*, 124(14):2271-2279 (2014).

Zhang et al., The $G_q$ and $G_{12}$ Families of Heterotrimeric G Proteins Report Selectivity, *Mol Pharmacol*, 75(1):235-241 (2009).

(56) References Cited

OTHER PUBLICATIONS

Akinwole et al., Unique odd-chain polyenoic Phospholipid fatty acids present in chytrid fungi, *Lipids*. 49:933-42 (2014).

Casas-Godoy et al., Yarrowla lipolytica lipase Lip2: An efficient enzyme for the production of concentrates of docosahexaenoic acid ethyl ester, *J. Biotechnol*. 180:30-6 (20141).

Irmisch et al., Altered serum mono- and polyunsaturated fatty acid levels in adults with ADHD, *ADHD Atten. Def. Hyp. Disord*. 5:303-11 (2013).

Kienberg, The synthesis of a number of "skipped" trienoic acids, *Arkiv for Kemi*. 23-32 (1967).

Klok et al., Synthesis of methyl (E,Z,Z,)-2(or 4 or 6), 9,12-octadecatrienoate and methyl (E,Z,Z)-2(or 6 or 8), 11, 14-eicosatrienoate, *Journal of the Royal Netherlands Chemical Society*. 132-7 (1980).

Porter et al., A new route to lipid hydroperoxides: orbital symmetry controlled ring opening of vinylcyclopropyl bromides, *J. Am. Chem. Soc*. 102:5912-3 (1980).

Ritskes-Hoitinga et al., The association of increasing dietary concentrations of fish oil with hepatotoxic effects and a higher degree of aorta atherosclerosis in the ad lib.-fed rabbit, *Food Chern. Toxicol*. 36:663-72 (1998).

Struijk et al., Specificity in the enzymic conversion of polyunsaturated fatty acids into prostaglandins, Recueil. 85:1233-50 (1966).

Syazwani et al., Low-cost solid catalyst derived from waste *Cyrtopleura costata* (Angel Wing Shell) for biodiesel production using microalgae oil, *Energy Conversation and Management*. 101:749-56 (2015).

van der Linde et al., Synthesis of 2-submitted cis-8, cis-11, cis-14-eicosatrienoic acids, precursors for 2-submitted prostaglandins, *Journal of the Royal Netherlands Chemical Society*. 257-61 (1975).

van der Wolf et al., A novel bromination for an unsaturated α-anion ester. Synthesis of 2-bromo-cis-8, cis-11, cis-14-eicosatrienoic acid, *Journal of the Royal Netherlands*. 72-74 (1977).

Verma, Understanding topoisomerase I and II in terms of QSAR, *Biorganic & Medicinal Chemistry*. 13:1059-67 (2005).

Yeung et al., 12(S)-HETrE, a 12-Lipoxygenase Oxylipin of Dihomo-γ-Linolenic Acid, Inhibits Thrombosis via Gas Signaling in Platelets, *Arterioscler. Thromb. Vasc. Biol*. 36:2068-77 (2016).

\* cited by examiner

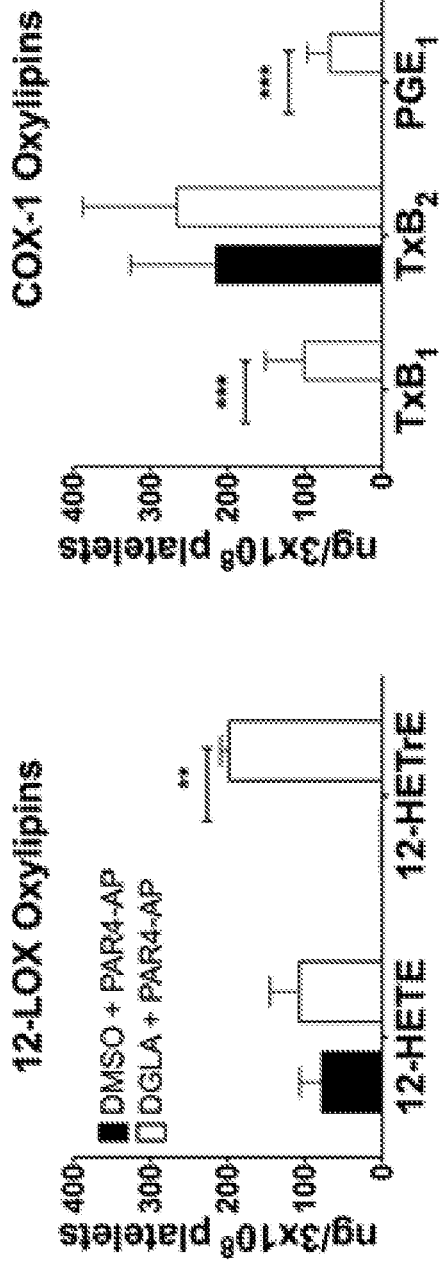
Figure 3A
Figure 3B
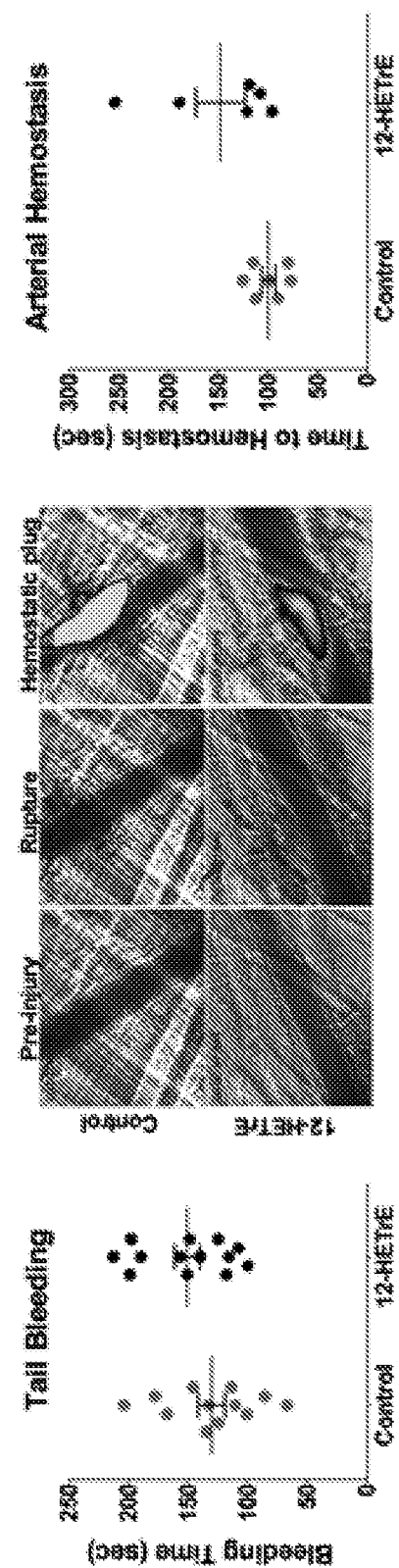
Figure 4A
Figure 4B

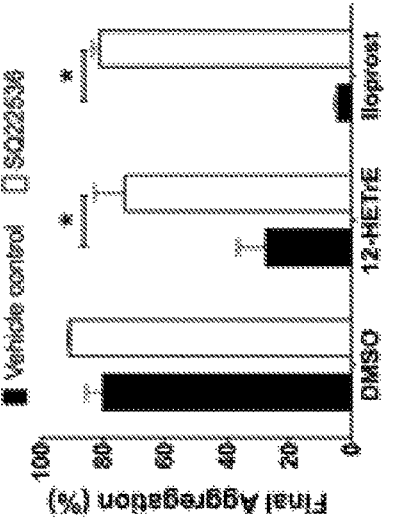
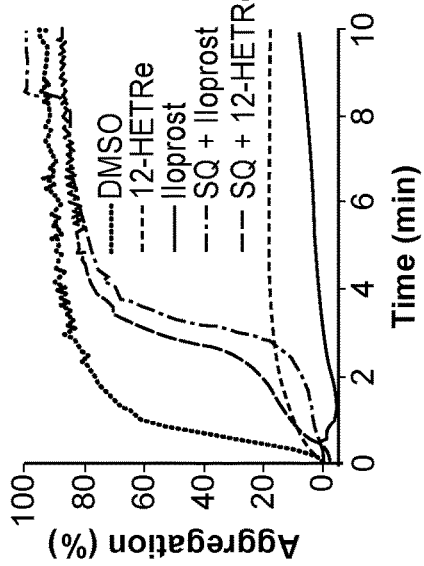
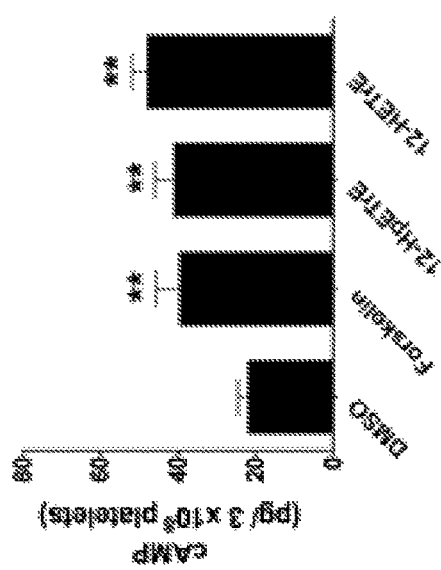
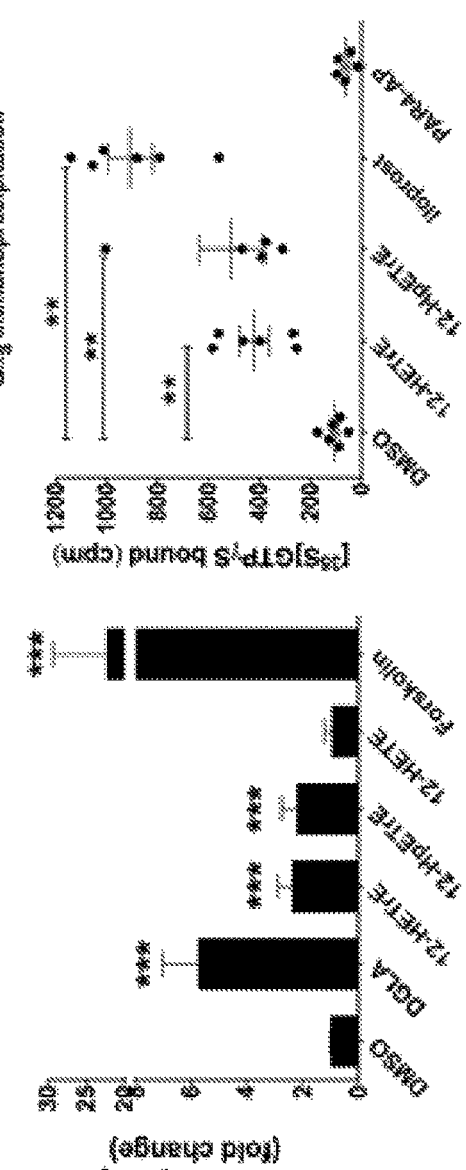
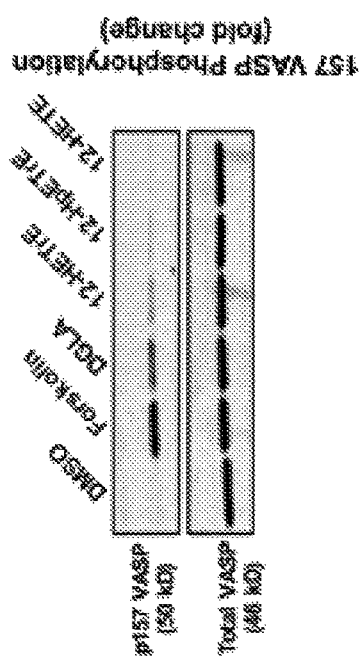
Figure 5A
Figure 5B
Figure 5C
Figure 5D

HYDROXYEICOSATRIENOIC ACID COMPOUNDS AND THEIR USE AS THERAPEUTIC AGENTS

CROSS-REFERENCE TO RELATED APPLICATION

This application claims the benefit of priority under 35 U.S.C. § 119(e) of U.S. Provisional Patent Application No. 62/353,917 filed Jun. 23, 2016, which is incorporated herein by reference.

STATEMENT OF GOVERNMENT INTEREST

This invention was made with government support under GM105671 awarded by the National Institutes of Health. The government has certain rights in the invention.

FIELD OF THE INVENTION

The present disclosure relates to 12(S)-hydroxyeicosatrienoic acid (12(S)-HETrE) compounds and prodrugs thereof, and their use as therapeutic agents.

BACKGROUND OF THE INVENTION

Platelet activation plays a critical role in the thrombotic complications associated with life-threatening cardiovascular ischemic events, such as myocardial infarction and stroke. Inhibiting platelet activation in individuals at risk for thrombotic events through the use of aspirin and $P2Y_{12}$ receptor antagonists has significantly decreased morbidity and mortality associated with these debilitating conditions (Chen et al., *Lancet* 366:1607-1621, 2005; Palacio et al., *Stroke* 43:2157-2162, 2012).

Polyunsaturated fatty acids (PUFAs) as a dietary supplement are commonly used for their potential cardioprotective effects, including their antiplatelet effects. Dihomo-γ-linolenic acid (DGLA), an ω-6 PUFA, has been shown to inhibit platelet aggregation ex vivo (Farrow and Willis, *Br J Pharmacol* 55:316P-317P, 1975; Kernoff et al., *Br Med J* 2:1441-1444, 1977; Willis et al., *Prostaglandins* 8:509-519, 1974). In addition, platelets isolated from humans, as well as baboons, rabbits, and rats that received daily oral doses of DGLA had a significant reduction in ex vivo aggregation. PUFAs are primarily thought to exert their regulatory effects on platelet function through their conversion into bioactive lipids (oxylipins) by oxygenases (Wada et al., *J Biol Chem* 282:22254-22266, 2007). In platelets, DGLA can be oxidized by cyclooxygenase-1 (COX-1) or platelet 12-lipoxygenase (12-LOX) (Falardeau et al., *Biochim Biophys Acta* 441:193-200, 1976) following its release from the phospholipid bilayer predominately through the actions of cytoplasmic phospholipase $A_2$ (Borsch-Haubold et al., *The Journal of biological chemistry* 270:25885-25892, 1995; Lands and Samuelsson, *Biochim Biophys Acta* 164:426-429, 1968). While both COX-1 and 12-LOX are able to oxidize DGLA to their respective metabolites, the relative contributions of these oxylipid products to the inhibitory effects of DGLA on platelet function remain unclear. Historically, the antiplatelet effects of DGLA have been attributed solely to COX-1-derived metabolites that have been shown to inhibit platelet activation (Farrow and Willis, supra; Kernoff et al., supra; Srivastava, *Z Ernahrungswiss* 17:248-261, 1978; Willis et al., supra). However, the DGLA derived products of COX-1 ($TXA_1$ and $PGE_1$) are labile and produced in low amounts in platelets (Bunting et al., *Prostaglandins* 12:897-913, 1976a; Bunting et al., *Br J Pharmacol* 56:344P-345P, 1976b; Moncada et al., *Nature* 263:663-665, 1976; Needleman et al., *Prostaglandins* 19:165-181, 1980).

Advances in antiplatelet therapy have significantly decreased the risk for morbidity and mortality due to thrombosis. However, even with the current standard-of-care antiplatelet therapies available, myocardial infarction and stroke due to occlusive thrombotic events remains one of the primary causes of morbidity and mortality globally. The fact that the rate of ischemic events still remains high in individuals on antiplatelet agents (Diener et al., *Lancet* 364:331-337, 2004) stresses the unmet clinical need for alternative therapies that reduce occlusive thrombotic events without promoting an increased risk of bleeding. Additionally, while traditional anti-platelet therapy has been useful for limiting platelet activation, its utility in disorders involving immune-targeting of the immune receptors on the platelet, such as immune thrombocytopenia (ITP), has been limited due to its propensity to cause bleeding and limited ability to prevent or inhibit platelet clearance. For these reasons, thrombotic disorders leading to platelet clearance, thrombosis, and bleeding remain a challenge to treat therapeutically.

SUMMARY OF THE INVENTION

The present disclosure relates to 12(S)-HETrE compounds and prodrugs, and their use as therapeutic agents, e.g., to prevent thrombosis and ischemia and treat thrombotic disorders.

In one aspect, the present disclosure provides a compound of Formula (0), or a pharmaceutically acceptable salt thereof:

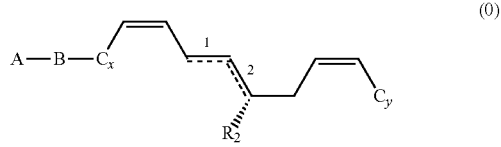

wherein: A is $-COOR^1$, $-OSO_3R^1$, $-OPO_3(R^1)_2$, or -G-HET; each $R^1$ independently is H or $C_{1-6}$alkyl; $R^2$ is H or OH; each ---- is a single or double bond, provided that (i) when ---- at bond 2 is a single bond, then ---- at bond 1 is a trans double bond and $R^2$ is OH, and (ii) when ---- at bond 1 is a single bond, then ---- at bond 2 is a cis double bond and $R^2$ is H. HET is an unsubstituted or substituted 5 to 10-membered heteroaryl group having 1, 2, 3, or 4 heteroatoms selected from the group consisting of N, S, or O; G is O, S, NH, or absent; $C_x$ is an alkylene group having x carbon atoms; $C_y$ is an alkyl group having y carbon atoms; x is 3, 4, 5, 6, or 7; y is 4, 5, 6, 7; and each carbon atom of the compound of Formula (0) independently is unsubstituted or substituted with one or more deuterium or fluorine atoms; with the proviso that when x is 6, y is 5, and each carbon atom of Formula (0) is unsubstituted, then A is not —COOH.

In some aspects, the compound of Formula (0) has a Formula (I):

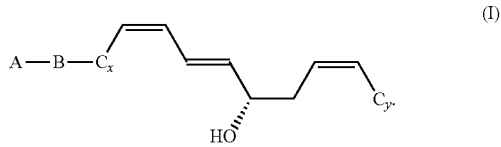

For example, the compound of Formula (I) can be selected from compounds (Ia), (Ib), (Ic), (Id), (Ie), (If), (Ig), (Ih), and (Ii), as described herein.

In some aspects, the compound of Formula (0) has a Formula (II):

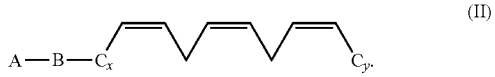

(II)

For example, the compound of Formula (II) can be selected from compounds (IIa), (IIb), (IIc), (IId), and (IIe) as described herein.

In another aspect, the present disclosure provides a composition comprising a therapeutically effective amount of a compound of Formula (I), Formula (II) or

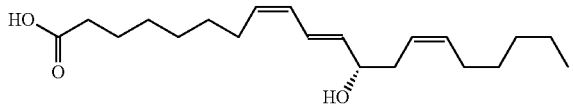 [SMILES: CCCCC/C=C\C[C@H](O)/C=C/C=C\CCCCCCC(=O)O]

(12(S)hydroxy-8Z-10E,14Z-eicosatrienoic acid), or a pharmaceutically acceptable salt of any of the foregoing, and a pharmaceutically acceptable carrier.

In still another aspect, the present disclosure provides a method of treating a thrombotic disorder or preventing thrombosis in a subject in need thereof comprising administering 12(S)-HETrE, a compound of Formula (0), a compound of Formula (I), a compound of Formula (II), or a pharmaceutically acceptable salt of any of the foregoing, or a composition comprising the same, to the subject in an amount effective to inhibit thrombus formation while maintaining hemostasis. In another aspect, the present disclosure provides a method of treating thrombocytopenia in a subject in need thereof comprising administering 12(S)-HETrE, a compound of Formula (0), a compound of Formula (I), a compound of Formula (II), a pharmaceutically acceptable salt of any of the foregoing, or a composition comprising the same, to the subject in an amount effective to prevent or inhibit loss of platelet cells.

In some aspects, the subject suffers from a thrombotic disorder selected from arterial thrombosis, deep vein thrombosis, pulmonary embolism, ischemic stroke, immune thrombocytopenia (ITP), Heparin-induced thrombocytopenia (HIT), and Heparin-induced thrombocytopenia and thrombosis (HITT), and/or is undergoing a surgical procedure.

The foregoing summary is not intended to define every aspect of the invention, and other features and advantages of the present disclosure will become apparent from the following detailed description, including the drawings. The present disclosure is intended to be related as a unified document, and it should be understood that all combinations of features described herein are contemplated, even if the combination of features are not found together in the same sentence, paragraph, or section of this disclosure. In addition, the disclosure includes, as an additional aspect, all embodiments of the invention narrower in scope in any way than the variations specifically mentioned above. With respect to aspects of the disclosure described or claimed with "a" or "an," it should be understood that these terms mean "one or more" unless context unambiguously requires a more restricted meaning. With respect to elements described as one or more within a set, it should be understood that all combinations within the set are contemplated. If aspects of the disclosure are described as "comprising" a feature, embodiments also are contemplated "consisting of" or "consisting essentially of" the feature. Additional features and variations of the disclosure will be apparent to those skilled in the art from the entirety of this application, and all such features are intended as aspects of the disclosure.

BRIEF DESCRIPTION OF THE DRAWINGS

(FIG. 1C) Active Rap1 (Rap1-GTP) was selectively precipitated from the lysates of platelets isolated from WT or 12-LOX$^{-/-}$ mice incubated with vehicle control or 10 µM DGLA (n=3 to 4 mice) prior to stimulation with increasing concentrations of PAR4-AP (50, 100, and 200 µM). Active Rap1 was normalized to the total amount of Rap1 in each sample, and each bar graph represents a percentage of vehicle control for each PAR4-AP concentration. Data represent mean±SEM. P<0.01, *P<0.001 two-tailed unpaired t-test. (FIG. 1D) Representative images of laser-induced injury of the cremaster arterioles, fluorescent platelet and fibrin accumulation monitored in real-time to assess thrombus growth in the WT vehicle control (n=3 mice, 10-15 thrombi per mouse), DGLA treated group (n=3 mice, 10-15 thrombi per mouse), 12-LOX$^{-/-}$ vehicle control (n=3 mice, 10-15 thrombi per mouse), and 12-LOX$^{-/-}$ treated with DGLA (n=3 mice, 10-15 thrombi per mouse). Scale bar: 40 µm. Mean fluorescence intensity (MFI) of platelet and fibrin accumulation at the site of injury were recorded over time in (FIG. 1E) WT and (FIG. 1F) 12-LOX$^{-/-}$ mice. Data represents mean±SEM; two-way ANOVA.

(FIG. 2C) Active Rap1 (Rap1-GTP) was selectively precipitated from the lysates of platelets isolated from WT or 12-LOX$^{-/-}$ mice incubated with vehicle control or 25 µM 12-HETrE (n=3 to 4 mice) prior to stimulation with increasing concentrations of PAR4-AP (50, 100, and 200 µM). Active Rap1 was normalized to the total amount of Rap1 in each sample, and each bar graph represents a percentage of vehicle control for each PAR4-AP concentration. Data represent mean±SEM. *P<0.05, P<0.01, *P<0.001 two-tailed unpaired t-test. (FIG. 2D) Representative images of laser-induced injury of the cremaster arterioles, fluorescent platelet and fibrin (red) accumulation monitored in real-time to assess thrombi growth in the WT vehicle control (n=3 mice, 10-15 thrombi per mouse), 12-HETrE treated group (n=3 mice, 10-15 thrombi per mouse, 10-15 thrombi per mouse), 12-LOX$^{-/-}$ vehicle control (n=3-4 mice, 10-15 thrombi per mouse), and 12-LOX$^{-/-}$ treated with 12-HETrE (n=3 mice, 10-15 thrombi per mouse). 12-LOX$^{-/-}$ vehicle control data is the same set as 12-LOX$^{-/-}$ vehicle control used for 12-LOX$^{-/-}$ DGLA treated comparison in FIG. 1F. Scale bar: 40 μm. Mean fluorescence intensity (MFI) platelet and fibrin accumulation at the site of injury were recorded over time in (FIG. 2E) WT and (FIG. 2F) 12-LOX$^{-/-}$ mice. Data represents mean±SEM; two-way ANOVA.

FIGS. 3A and 3B show that exogenous DGLA enhances platelet production of metabolites. (FIG. 3A) 12-LOX and (FIG. 3B) COX-1 metabolites from washed human platelets (n=7) treated with DGLA (10 μM) or DMSO for 10 minutes prior to stimulation with PAR4-AP (200 μM) were detected using mass spectrometry. Data represents mean±SEM; P<0.01,*P<0.001 two-tailed unpaired t-test.

FIGS. 4A to 4C show that hemostasis is not affected by 12(S)-HETre. Mice retro-orbitally injected with DMSO or 12-HETrE dissolved in saline prior to tail-bleeding. (FIG. 4A) Mean tail-bleeding time of control (n=12) or 12-HETrE (n=13) treated mice is denoted by the horizontal line. Arterial hemostasis induced by laser-induced puncturing of the cremaster muscle arterioles was performed to assess the kinetics of hemostatic plug formation. (FIG. 4B) Representative images of hemostatic plug formation, composed of fluorescent platelets and fibrin were acquired over time. Blue arrows denote the site of vessel rupture and leakage of RBCs. (FIG. 4C) Time to form hemostatic plug in control (n=7) and 12-HETrE (n=6) mice as assessed by RBC leakage. Data represent mean±SEM; two-tailed unpaired t-test.

FIGS. 5A to 5D show that 12(S)-HETrE activates adenylyl cyclase-mediated signaling by 12(S)-HETrE in platelets. (FIG. 5A) Mass spectrometry quantification of cAMP was performed on lysed washed human platelets (n=5) that were pre-treated with 10 μM of a phosphodiesterase inhibitor, 3-isobutyl-1methylxanthine (IBMX), for 30 minutes prior to incubation with DMSO, 12-HETrE (25 μM), 12-HpETrE (25 μM), or forskolin (0.5 μM), an adenylyl cyclase activator, for 1 minute. (FIG. 5B) Washed human platelets (n=4) were pre-treated with an adenylyl cyclase inhibitor, SQ22536 (25 μM), or DMSO for 20 minutes and then incubated with 12-HETrE (7.5 to 25 μM) or iloprost (0.2 to 0.4 nM) for 1 minute prior to stimulation. Platelet aggregation induced by an EC$_{80}$ concentration of PAR4-AP (35 to 50 μM) was measured for 10 minutes. Representative tracings of aggregation are shown on the left and bar graphs of the final aggregation of four independent experiments are shown on the right. (FIG. 5C) To measure VASP phosphorylation, western blot analysis was performed on lysates from washed human platelets (n=8) incubated with DMSO, DGLA (10 μM), 12-HETrE (25 μM), 12-HpETrE (25 μM), or forskolin (0.5 μM) for 1 minute using antibodies specific for phospho-VASP (p157 VASP) or total VASP. Phosphorylated VASP was normalized to total VASP and DMSO for fold change in 157 VASP phosphorylation. (FIG. 5D) Gα$_s$ was immunoprecipitated following incubation of human platelet membranes with DMSO, 12-HETrE (25 μM), 12-HpETrE (25 μM), Iloprost (10 μM) or PAR4-AP in the presence of [$^{35}$S]GTPγS. The immunoprecipitates (n=6) were then counted and background counts from normal IgG controls were subtracted. Data represent mean±SEM. *P<0.05, P<0.01, *P<0.001, two-tailed unpaired t-test.

DETAILED DESCRIPTION OF THE INVENTION

Figure 1A:
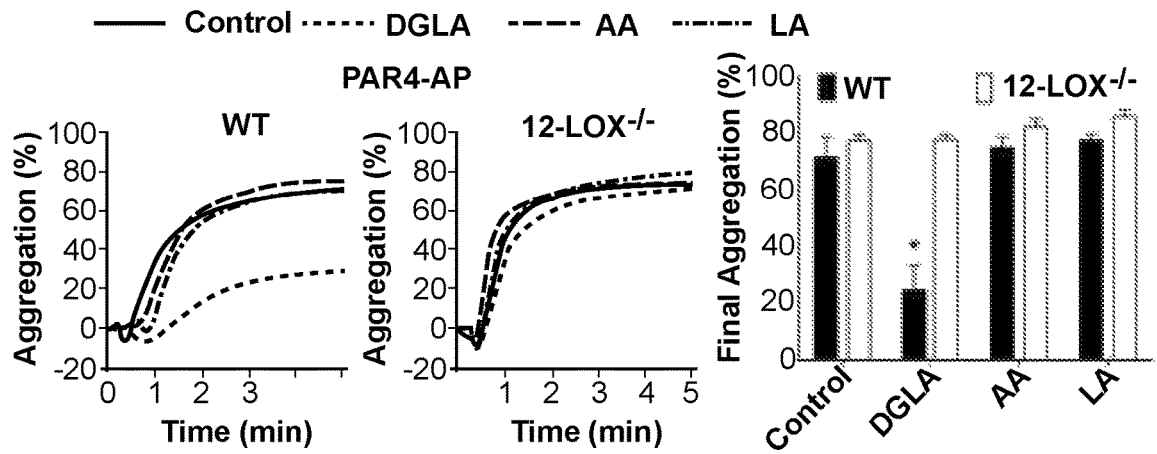
FIGS. 1A to 1F show that 12-LOX is required for DGLA inhibition of platelet aggregation and thrombus formation. Representative tracings and combined aggregation data of (FIG. 1A) WT (n=4) or (FIG. 1B) 12-LOX$^{-/-}$ (n=4) platelets stimulated with $EC_{80}$ concentration of PAR4-AP (WT 100 µM; 12-LOX$^{-/-}$ 200 µM) or collagen (WT 5 µg/mL; 12-LOX$^{-/-}$ 2 or 5 µg/mL) in the presence or absence of 10 µM of PUFAs (DGLA, AA, or LA). Aggregation was monitored for 10 minutes. Data represents mean±SEM. *P<0.05 two-tailed unpaired t-test.

The present disclosure relates to 12(S)-HETrE compounds and prodrugs thereof that have antiplatelet activity and are useful for treating thrombotic disorders, e.g., by preventing or inhibiting thrombosis, thrombocytopenia, and/or ischemia, without disrupting hemostasis. The compounds and methods of the present disclosure impair thrombus formation in vivo, providing cardioprotective effects through the attenuation of platelet function. Unlike other antiplatelet agents that cause excessive bleeding (Ahrens and Peter, *Nat Biotechnol* 26:62-63, 2008; Capodanno et al., *J Am Coll Cardiol* 66:1639-1640, 2015; Lee et al., *Br J Pharmacol* 166:2188-2197, 2012), the compounds and methods of the present disclosure do not significantly alter hemostasis and instead exert an anti-thrombotic effect, while at the same time maintaining primary hemostasis.

The following definitions may be useful in aiding the skilled practitioner in understanding the disclosure. Unless otherwise defined herein, scientific and technical terms used in the present disclosure shall have the meanings that are commonly understood by those of ordinary skill in the art.

As used herein, the term "alkyl" refers to straight-chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_{1-7}$ alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Non-limiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

As used herein, the term "alkenyl" is defined identically as "alkyl" except for containing at least one carbon-carbon double bond, and having two to thirty carbon atoms, for example, two to twenty carbon atoms, or two to ten carbon atoms. The term $C_n$ means the alkenyl group has "n" carbon atoms. For example, $C_4$ alkenyl refers to an alkenyl group that has 4 carbon atoms. $C_2$-$C_7$ alkenyl refers to an alkenyl group having a number of carbon atoms encompassing the entire range (i.e., 2 to 7 carbon atoms), as well as all subgroups (e.g., 2-6, 2-5, 3-6, 2, 3, 4, 5, 6, and 7 carbon atoms). Specifically contemplated alkenyl groups include ethenyl, 1-propenyl, 2-propenyl, and butenyl. Unless otherwise indicated, an alkenyl group can be an unsubstituted alkenyl group or a substituted alkenyl group.

As used herein, the term "alkylene" refers to an alkyl group having a substituent. The term $C_n$ means the alkylene group has "n" carbon atoms. For example, $C_{1-6}$ alkylene refers to an alkylene group having a number of carbon atoms encompassing the entire range, as well as all subgroups, as previously described for "alkyl" groups.

As used herein, the term "cycloalkyl" refers to an aliphatic cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_{5-8}$ cycloalkyl refers to cycloalkyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Non-limiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group. The cycloalkyl groups described herein can be isolated or fused to another cycloalkyl group, a heterocycloalkyl group, an aryl group and/or a heteroaryl group.

As used herein, the term "aryl" refers to monocyclic or polycyclic (e.g., fused bicyclic and fused tricyclic) carbocyclic aromatic ring systems. Non-limiting examples of aryl groups include, phenyl, naphthyl, tetrahydronaphthyl, phenanthrenyl, biphenylenyl, indanyl, indenyl, anthracenyl, and fluorenyl. Unless otherwise indicated, an aryl group can be an unsubstituted aryl group or a substituted aryl group.

As used herein, the term "heteroaryl" refers to monocyclic or polycyclic (e.g., fused bicyclic and fused tricyclic) aromatic ring systems, wherein one to four-ring atoms are selected from oxygen, nitrogen, or sulfur, and the remaining ring atoms are carbon, said ring system being joined to the remainder of the molecule by any of the ring atoms. Non-limiting examples of heteroaryl groups include pyridyl, pyrazinyl, pyrimidinyl, pyrrolyl, pyrazolyl, imidazolyl, thiazolyl, triazolyl, tetrazolyl, oxazolyl, isoxazolyl, thiadiazolyl, oxadiazolyl, furanyl, quinolinyl, isoquinolinyl, benzoxazolyl, benzimidazolyl, and benzothiazolyl. Unless otherwise indicated, a heteroaryl group can be an unsubstituted heteroaryl group or a substituted heteroaryl group.

As used herein, the term "alkoxy" or "alkoxyl" as used herein refers to a "—O-alkyl" group. The alkoxy or alkoxyl group can be unsubstituted or substituted.

As used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, ether, polyether, thioether, polythioether, aryl, heteroaryl, hydroxyl, oxy, alkoxy, heteroalkoxy, aryloxy, heteroaryloxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms. A substituted chemical functional group can itself include one or more substituents.

As used herein, the term "12(S)-HETrE compounds" refers to 12(S)-hydroxyeicosatrienoic acid, e.g., 12(S)-hydroxy-8Z,10E,14Z-eicosatrienoic acid, and analogs thereof, including the compounds of Formula (0) and Formula (I) described herein, as well as pharmaceutically acceptable salts of any of the foregoing, and prodrug compounds that are metabolized to 12(S)-hydroxyeicosatrienoic acid in vivo, including the compounds of Formula (II) described herein and pharmaceutically acceptable salts thereof.

The terms "therapeutically effective amount" and "effective amount" depend on the condition of a subject and the specific compound(s) administered. The terms refer to an amount effective to achieve a desired biological, e.g., clinical, effect. A therapeutically effective amount varies with the nature of the disease being treated, the length of time that activity is desired, and the age and the condition of the subject. In some aspects, a therapeutically effective amount of a compound or composition of the disclosure is an amount effective to prevent or inhibit thrombus (blood clot) formation, reduce thrombus size, decrease thrombus stability, prevent thrombosis, prevent or inhibit low platelet count (thrombocytopenia), increase or maintain blood flow in a target area, and/or inhibit platelet activation/aggregation.

As used herein, the terms "patient" and "subject" may be used interchangeably and mean animals, such as dogs, cats, cows, horses, and sheep (i.e., non-human animals) and humans.

As used herein, the term "pharmaceutically acceptable" means that the referenced substance, such as a compound of the present disclosure, or a composition containing the compound, or a particular excipient, are safe and suitable for administration to a patient. The term "pharmaceutically acceptable carrier" refers to a medium that does not interfere with the effectiveness of the biological activity of the active ingredient(s) and is not toxic to the host to which it is administered.

As used herein, the term "excipient" means any pharmaceutically acceptable additive, carrier, diluent, adjuvant, or other ingredient, other than the active pharmaceutical ingredient (API).

As used herein the terms "treating", "treat" or "treatment" and the like include preventative (e.g., prophylactic) and palliative treatment.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

In one aspect, the present disclosure provides a compound of Formula (0), or a pharmaceutically acceptable salt thereof:

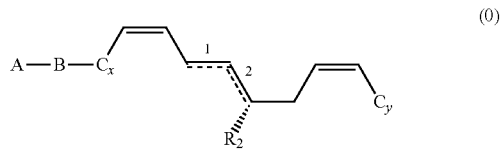

(0)

wherein: A is —COOR$^1$, —OSO$_3$R$^1$, —OPO$_3$(R$^1$)$_2$, or -G-HET; R$^1$ is H or C$_{1-6}$alkyl; R$^2$ is H or OH; each ---- is a single or double bond, provided that (i) when ---- at bond 2 is a single bond, then ---- at bond 1 is a trans double bond and $R^2$ is OH, and (ii) when ---- at bond 1 is a single bond, then ---- at bond 2 is a cis double bond and $R^2$ is H; HET is an unsubstituted or substituted 5 to 10-membered heteroaryl group having 1, 2, 3, or 4 heteroatoms selected from the group consisting of N, S, or O; G is O, S, NH, or absent; $C_x$ is an alkylene group having x carbon atoms; $C_y$ is an alkyl group having y carbon atoms; x is 3, 4, 5, 6, or 7; y is 4, 5, 6, 7; and each carbon atom of the compound of Formula (0) independently is unsubstituted or substituted with one or more deuterium or fluorine atoms; with the proviso that when x is 6, y is 5, and each carbon atom of Formula (0) is unsubstituted, then A is not COOH.

In some embodiments, A is —COOR$^1$. In various embodiments, A is —OSO$_3$R$^1$. In some cases, A is —OPO$_3$(R$^1$)$_2$. In some cases, R$^1$ is H, and A is —COOH, —OSO$_3$H, or —OPO$_3$H$_2$. In various cases, R$^1$ is C$_{1-6}$alkyl or C$_{1-4}$alkyl (e.g., H, Me, Et, Pr, $^i$Pr, Bu, $^s$Bu, $^t$Bu). For example, A can be —COOMe, —COOEt, —OSO$_3$Me, —OSO$_3$Et, —OPO$_3$Me$_2$, or —OPO$_3$Et$_2$. In some embodiments, A is -G-HET. HET can be any 5- or 6-membered heteroaryl group having 1, 2, 3, or 4 heteroatoms selected from the group consisting of N, S, or O. Non-limiting examples of suitable heteroaryl groups include pyridyl, pyrazinyl, pyrimidinyl, pyrrolyl, pyrazolyl, imidazolyl, thiazolyl, triazolyl, tetrazolyl, oxazolyl, isoxazolyl, thiadiazolyl, oxadiazolyl, furanyl, quinolinyl, isoquinolinyl, benzoxazolyl, benzimidazolyl or benzothiazolyl. In some embodiments, the heteroaryl group is selected from tetrazolyl, triazolyl, and isoxazolyl. In some cases, HET is unsubstituted. In various embodiments, HET is substituted, such as with one or more hydroxyl or alkoxyl groups (e.g., OMe, OEt, OPr, OBt). In some cases, G is absent. In various cases, G is O. In some embodiments, G is S. In various embodiments, G is NH. For example, G-HET can include

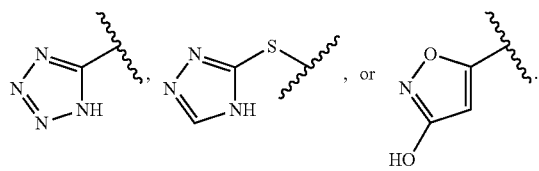 [SMILES: *c1nnn[nH]1 ; *Sc1nnc[nH]1 ; *c1cc(O)no1]

In some embodiments, x is 3. In some cases, x is 4. In various embodiments, x is 5. In various cases, x is 6. In some cases, x is 7. For example, x can be 4, 5, or 6. In some embodiments, y is 4. In some cases, y is 5. In various embodiments, y is 6. In various cases, y is 7. For example, y can be 4, 5, or 6. Combinations of x and y can include the following:

| x | y |
|---|---|
| 3 | 4 |
| 3 | 5 |
| 3 | 6 |
| 3 | 7 |
| 4 | 4 |
| 4 | 5 |
| 4 | 6 |
| 4 | 7 |
| 5 | 4 |
| 5 | 5 |
| 5 | 6 |
| 5 | 7 |
| 6 | 4 |
| 6 | 5 |
| 6 | 6 |
| 6 | 7 |
| 7 | 4 |
| 7 | 5 |
| 7 | 6 |
| 7 | 7 |

In some cases, ---- at bond 2 is a single bond, ---- at bond 1 is a trans double bond and $R^2$ is OH. In these cases, the compound of Formula (0) has a Formula (I):

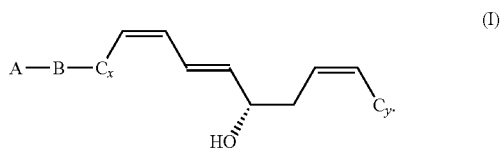

Compounds of Formula (I) are analogs of 12(S)-HETrE and can be used as therapeutic agents, e.g., to prevent thrombosis and ischemia and treat thrombotic disorders, as described herein.

In some embodiments, ---- at bond 1 is a single bond, ---- at bond 2 is a cis double bond, and $R^2$ is H. In these embodiments, the compound of Formula (0) has a Formula (II):

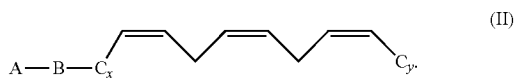

Compounds of Formula (II) can act as prodrugs of compounds of Formula (I). In some embodiments, compounds of Formula (II) can be metabolized in vivo to compounds of Formula (I) through deprotonation at position 10 and hydroxylation at position 12.

In some cases, at least one carbon atom of Formula (0), Formula (I), or Formula (II) is substituted with a deuterium atom. In various cases, the carbon atom at position 13 is disubstituted with deuterium atoms. For example, the carbon atom at position 13 of Formula (I) can be disubstituted with deuterium atoms, as shown below:

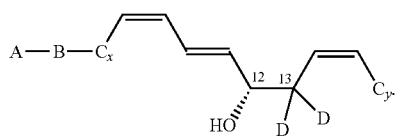

In some embodiments, each carbon atom of Formula (0), Formula (I), or Formula (II) is mono- or disubstituted with deuterium atoms. In some cases, at least one carbon atom of Formula (0), Formula (I), or Formula (II) is substituted with a fluorine atom. In various cases, the carbon atom at position 13 is disubstituted with fluorine atoms. For example, the carbon atom at position 13 of Formula (I) can be disubstituted with fluorine atoms, as shown below:

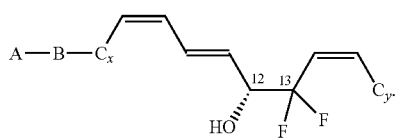

In some embodiments, each carbon atom of Formula (0), Formula (I), or Formula (II) is mono- or disubstituted with fluorine atoms. In embodiments wherein a carbon atom of Formula (I) is substituted with deuterium and/or fluorine, the 12(S)-hydroxyl group is never replaced with the deuterium or fluorine.

Examples of compounds of Formula (I) include:

(Ia)
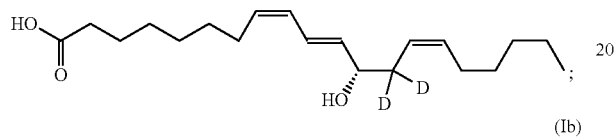

(Ib)
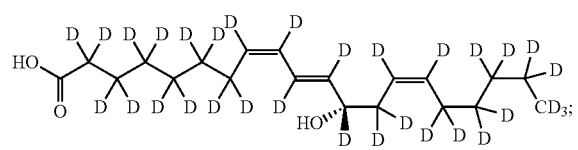

(Ic)
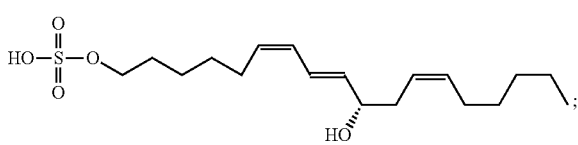

(Id)
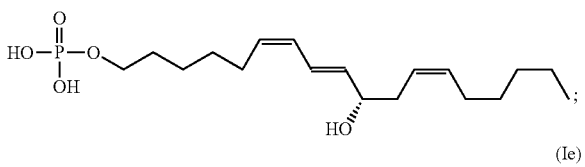

(Ie)
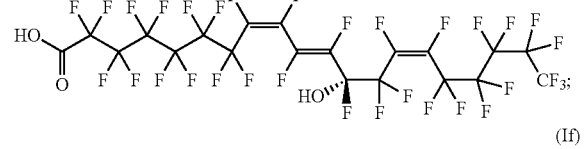

(If)
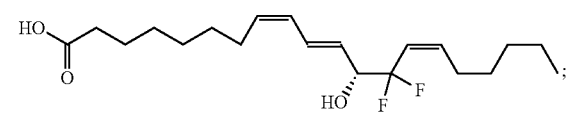

(Ig)
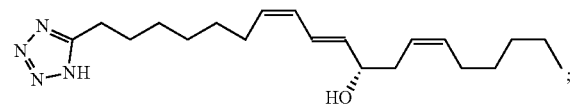

(Ih)
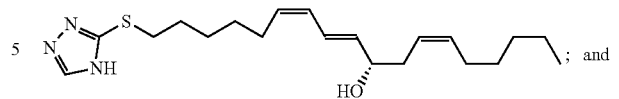
; and (Ii)
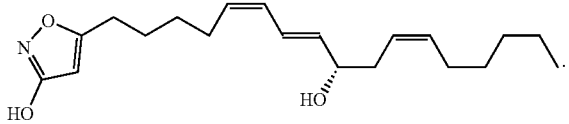
.

Examples of compounds of Formula (II) include:

(IIa)

(IIb)

(IIc)

(IId)
, and (IIe)
.

In some embodiments, the compound of Formula (II) is compound (IIa). In some cases, the compound of Formula (II) is compound (IIb). In various embodiments, the compound of Formula (II) is compound (IIc). In various cases, the compound of Formula (II) is compound (IId). In some embodiments, the compound of Formula (II) is compound (IIe).

The compounds of Formula (II) can be prepared by any method known to one skilled in the art. For example, the compounds of Formula (II) can be prepared by first tosylating commercially available γ-linoleyl alcohol under basic conditions with tosyl chloride, and then reacting the tosylate with a desired 5-membered heterocyclic ring having an exocyclic nucleophilic thiol group via a displacement reaction, as shown in the scheme, below.

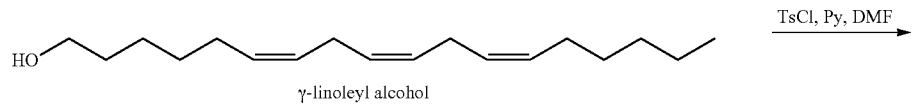

γ-linoleyl alcohol

-continued
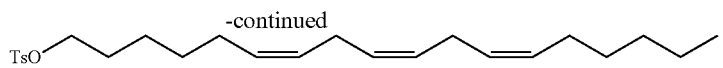

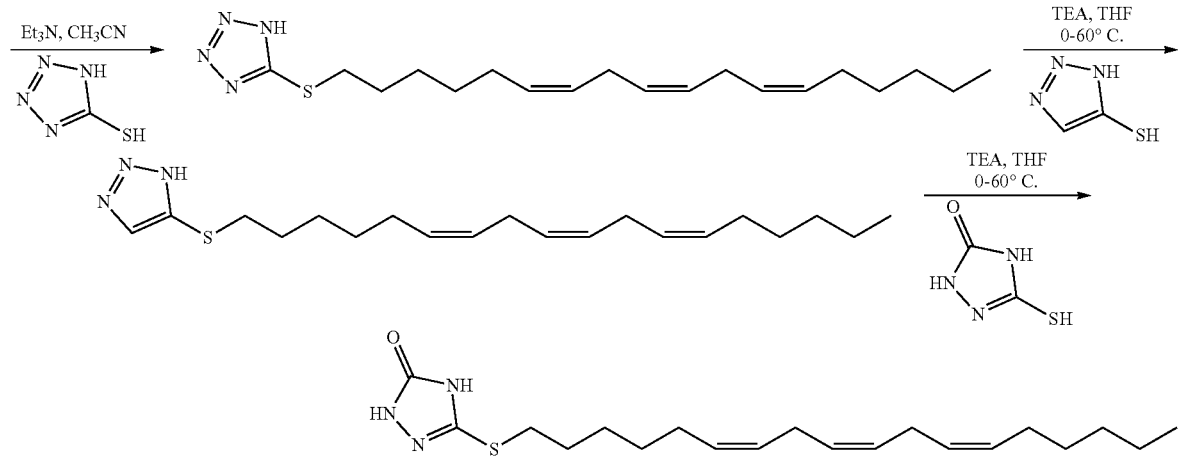

The compounds of Formula (I) can be prepared similarly to the compounds of Formula (II), except that the triene is oxygenated at the 12-position using methods commonly known to those skilled in the art to produce the 12(S)-stereoisomer. For example, to synthesize 12(S)-hydroxy-8Z, 10E, 14Z-eicosatrienoic acid (12(S)-HETrE), dihomo-γ-linolenic acid (DGLA) can undergo enzymatic oxidation with 12-lipoxygenase.

The present disclosure also provides a composition comprising an effective amount of a compound of Formula (0), a compound of Formula (I), a compound of Formula (II) or

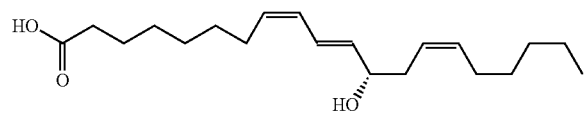 [SMILES: CCCCC/C=C\C[C@H](O)/C=C/C=C\CCCCCCC(=O)O]

(12(S)-hydroxy-8Z,10E,14Z-eicosatrienoic acid), or a pharmaceutically acceptable salt of any of the foregoing, and a pharmaceutically acceptable carrier. Pharmaceutically acceptable carriers include, but are not limited to, water, saline, phosphate buffered saline, and buffers. Preferably, the carrier is sterile. Other excipients, including buffering agents, dispersing agents, and preservatives, are known in the art and may be included in the composition. Further examples of components that may be employed in compositions are presented in Remington's Pharmaceutical Sciences, 16$^{th}$ Ed. (1980) and 20$^{th}$ Ed. (2000), Mack Publishing Company, Easton, Pa. A composition may be in any suitable dosage form including, but not limited to, tablets, capsules, implants, depots, liquids, patches, lozenges, creams, gels, ointments, lotions, sprays, and eye drops.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. The compositions may also include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate and/or one or more of: (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the compositions can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

In one aspect, a method of treating a thrombotic disorder in a subject in need thereof comprising administering a therapeutically effective amount of a compound or composition described herein to the subject is provided. In a further aspect, a method of treating a thrombotic disorder in a subject in need thereof also is provided comprising administering a therapeutically effective amount of a compound or composition described herein to the subject in an amount effective to inhibit thrombus formation while maintaining hemostasis, i.e., without increased risk of bleeding. In another aspect, a method of inhibiting thrombosis comprising contacting a platelet with an effective amount of a compound or composition described herein is provided. In another aspect, a method of treating thrombocytopenia in a subject is provided comprising administering a compound or composition described herein to the subject in an amount effective to prevent or inhibit loss of platelet cells. For example, a compound or composition described herein is administered in an amount effective to maintain or increase platelet count or to prevent or inhibit loss of platelet cells, resulting in a decrease in platelet count of less than about 5%, less than about 10%, less than about 15%, or less than about 20%, compared to pre-treatment.

In any of the foregoing methods, a compound or composition described herein is administered in an amount effective to inhibit platelet aggregation and/or platelet integrin activation. Without intending to be bound by theory, the antiplatelet effects of the 12(S)-HETrE compounds of the disclosure are believed to be mediated through the activation of the $G\alpha_s$ signaling pathway leading to formation of cAMP and PKA activation in the platelet. In some aspects, the compound or composition is administered in an amount effective to inhibit Rap1 activation, activate $G\alpha_s$-linked G-protein coupled receptors (GPCRs), activate cAMP, and/or activate protein kinase A (PKA). The 12(S)-HETrE compounds of the disclosure are distinct from 12(R)-hydroxy-5,8,14-eicosatrienoic acid (12(R)-HETrE), both in structure and physiological effects (Yeung and Holinstat, *Prostaglandins Other Lipid Mediat* available online Mar. 1, 2017).

In one aspect of the present methods, a therapeutically effective amount of a compound or composition described herein, typically formulated in accordance with pharmaceutical practice, is administered to a subject in need thereof. The ability of the compounds and compositions of the present disclosure to inhibit platelet activation, thrombocytopenia, and/or thrombus formation in a subject in need thereof provides therapeutic efficacy in treating a wide range of thrombotic disorders. In one aspect, the subject has a disease or disorder selected from the group consisting of arterial thrombosis, deep vein thrombosis, pulmonary embolism, ischemic stroke, immune thrombocytopenia (ITP), Heparin-induced thrombocytopenia (HIT), and Heparin-induced thrombocytopenia and thrombosis (HITT). One of ordinary skill will appreciate that treating a disease or disorder does not require complete eradication of the disease or disorder. Any beneficial physiologic response is contemplated, such as prevention of thrombus formation, inhibition of thrombus growth, prevention or inhibition of low platelet count (thrombocytopenia), reduction in thrombus size, improved blood flow, and the like. In another aspect, the subject is undergoing a surgical procedure, and a compound or composition of the disclosure is administered as a prophylactic measure before the surgical procedure or is administered during or after the surgical procedure, e.g., at an incision site, to prevent or control thrombosis.

In some aspects, therapeutic efficacy can be measured using coagulation tests and/or hemostasis tests known in the art to evaluate effects on thrombus formation, e.g., before and after administration of the compounds of the present disclosure. Examples of coagulation and hemostasis tests include, but are not limited to, complete blood counts (CBC), Factor (e.g., Factor II, V, VII, VIII, IX, X, XI, or XI) assays, von Willebrand Factor (vWF) tests, fibrinogen level measurements, prothrombin time tests, activated partial thromboplastin time tests, thrombin time tests, D-Dimer tests, platelet counts, platelet aggregometry tests, bleeding time tests, and coagulometers. Effects on platelet activation and aggregation, e.g., in the presence and absence of the compounds of the present disclosure, can also be measured using molecular biology techniques known in the art, including, but not limited to, ex vivo assays for cAMP formation, Rap1 activation, PKA activation, platelet aggregation, fluorescence labeling (e.g., of platelets and/or fibrin), and microscopy.

A particular administration regimen for a given subject will depend, in part, upon the compound or composition, the amount administered, the route of administration, and the cause and extent of any side effects. The amount administered to a subject (e.g., a mammal, such as a human) in accordance with the disclosure should be sufficient to effect the desired response over a reasonable time frame. Dosage typically depends upon the route, timing, and frequency of administration.

Purely by way of illustration, the methods of the present disclosure comprise administering, e.g., from about 0.1 mg/kg to about 50 mg/kg or more of a compound of the present disclosure based on the body weight of the subject, depending on the factors mentioned above. In some aspects, the dosage ranges from about 0.1 mg/kg to about 0.5 mg/kg, about 5 mg/kg to about 25 mg/kg, about 10 mg/kg to about 50 mg/kg, about 1 mg/kg to about 10 mg/kg, about 15 mg/kg to about 30 mg/kg, about 1 mg/kg to about 20 mg/kg, or about 10 mg/kg to about 25 mg/kg. In some aspect, the dosage of a compound is about 0.1 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, or about 50 mg/kg. In some aspects, a composition or method of the present disclosure comprises a dose of a compound described herein ranging from about 1 mg to about 500 mg, for example, about 1 mg to about 10 mg, about 25 mg to about 100 mg, about 50 mg to about 125 mg, about 200 mg to about 500 mg, or about 100 mg to about 300 mg. In some aspect, the dose of the compound is about 1 mg, about 5 mg, about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg. The dosage is administered as needed, for example, continuously, one to three times daily, every other day, twice a week, weekly, every two weeks, monthly, or less frequently. The above dosages are exemplary of the average case, but there can be individual instances in which higher or lower dosages are merited, and such are within the scope of this disclosure. The determination of dosage ranges and optimal dosages for a particular patient is within the ordinary skill in the art.

Suitable methods of administering a physiologically acceptable composition, such as a composition comprising a compound described herein, are well known in the art. Although more than one route can be used to administer a compound, a particular route can provide a more immediate and more effective reaction than another route. Depending on the circumstances, a compound or composition described herein is introduced into a surgical site, applied or instilled into a body cavity, absorbed through the skin or mucous membranes, inhaled, ingested and/or introduced into circulation. In one aspect, the compound or composition is administered orally. In another aspect, the compound or composition is injected intravenously and/or intraperitoneally. In still another aspect, the compound or composition is administered locally by directly contacting platelets with the compound or composition. For example, in certain circumstances, it will be desirable to deliver the composition through injection or infusion by intravenous, intratumoral, intraperitoneal, intracerebral (intra-parenchymal), intracerebroventricular, intramuscular, intraocular, intraarterial, intraportal, intralesional, intramedullary, intrathecal, intraventricular, transdermal, subcutaneous, intranasal, transdermal, enteral, topical, sublingual, urethral, vaginal, or rectal means; by controlled, delayed, sustained or otherwise modified release systems; or by implantation devices. Alternatively, the composition is administered via implantation of a matrix, membrane, sponge, or another appropriate material onto which the compound has been absorbed or encapsulated. Where an implantation device is used, the device is, in one aspect, implanted into any suitable tissue or organ, and delivery of the desired compound is, for example, via diffusion, timed-release bolus, or continuous administration.

The present disclosure will be more readily understood by reference to the following Example, which are provided by way of illustration and are not intended to be limiting.

EXAMPLES

Materials and Methods
Reagents.
Fatty acids: EPA, LA, AA, and DGLA (Nu-Chek), PAR4-AP (GL Biochem, Shanghai, China), collagen (Chronolog Corp.), Ultima Gold scintillation fluid (Perkin Elmer), [$^{35}$S]GTPγS (1250 Ci/mmol) (Perkin Elmer), GTP and GDP (Sigma-Aldrich), p-VASP (S-157) and Rap1 antibodies (Santa Cruz), total human and mouse VASP antibodies (Enzo Life Sciences Inc), glutathione sepaharose beads (GE Healthcare), secondary IRDye antibodies (LI-COR), Odyssey blocking buffer (LI-COR), acetylsalicylic acid (aspirin) (Sigma-Aldrich), Pierce Protein A Plus Agarose (Thermo Fisher Scientific), forskolin (AG Scientific), 3-isobutyl-1methylxanthine (Sigma-Aldrich), Sepharose 2B (Sigma-Aldrich), SQ 22536 (Tocris), DyLight 488 anti-GPIb antibody (Emfret), calcein acetoxymethyl ester (Calcein-AM) (Molecular Probes), Alexa647-labeled antibody recognizing fibrin (a kind gift from Dr. R. Camire from Children's Hospital of Philadelphia). Lipid standards: 9,11,15-trihydroxy-thrombox-13-en-1-oic acid (TxB$_1$), 9α,11,15S-trihydroxy-thromboxa-5Z,13E-dien-1-oic acid (TxB$_2$), 9α,11,15S-trihydroxy-thromba-5Z,13E-dien-1-oic-3,3,4,4-d$_4$ acid (TxB$_2$-d$_4$), 9-oxo-11α,15S-dihydroxy-prost-13E-en-1-oic acid (PGE$_1$), 9-oxo-11α,15S-dihydroxy-prosta-5Z,13E-dien-1-oic acid (PGE$_2$), 9-oxo-11α, 15S-dihydroxy-prost-13E-en-1-oic-3,3,4,4-d$_4$ acid (PGE$_1$-d$_4$), 9-oxo-11α,15S-dihydroxy-prosta-5Z,13E-dien-1-oic-3,3,4,4-d$_4$ acid (PGE$_2$-d$_4$), 12(S)-hydroxy-5Z,8Z,10E,14Z-eicosatetraenoic-5, 6,8,9,11,12,14,15-d$_8$ acid (12(S)HETE-d$_8$), and 13S-hydroxy-9Z,11E-octadecadienoic-9,10,12, 13-d$_4$ acid (13(S)HODE-d$_4$) (Cayman Chemical), 12-hydroxy-5Z,8Z,10E,14Z-eicosatetraenoic (12HETE), 12(S)-hydroxy-8Z, 10E,14Z-eicosatrienoic acid (12(S)-HETrE), 12-hydroxy-5Z, 8Z, 10E, 14Z, 17Z-eicosapentaenoic acid (12-HEPE) standards were biosynthesized as described previously (Ikei et al., *J Lipid Res* 53:2546-2559, 2012).

Synthesis of 5-(((6Z,9Z,12Z)-octadeca-6,9,12-trien-1-yl)thio)-2,4-dihydro-3H-1,2,4-triazol-3-one (Compound IIc)

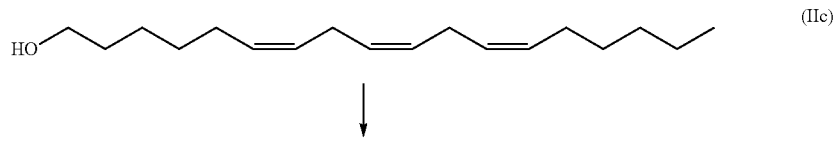

(IIc)

↓

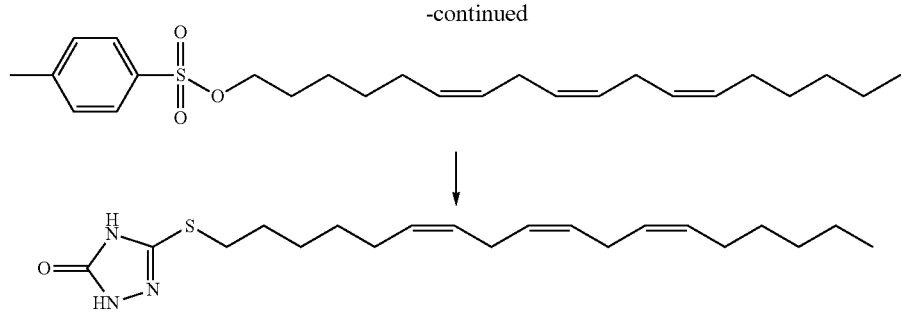

Compound IIc was synthesized in two steps. First, 4-methylbenzenesulfonyl chloride (140 mg, 0.71 mmol) was added to a solution of (6Z,9Z,12Z)-octadeca-6,9,12-trien-1-ol (94 mg, 0.36 mmol) in pyridine (2 ml). The reaction stirred at room temperature for 4 h. The reaction mixture was concentrated to dryness, then purified by column chromatography eluting with 100% hexanes until least polar spot had eluted, then switched to 5% ethyl acetate in hexanes to provide the (6Z,9Z,12Z)-octadeca-6,9,12-trien-1-yl 4-methylbenzenesulfonate as a clear, colorless oil (66 mg, 44%). $^1$H NMR (500 MHz, Chloroform-d) δ ppm 7.88-7.72 (m, 2H), 7.41-7.31 (m, 2H), 5.51-5.19 (m, 6H), 4.02 (t, J=6.5 Hz, 2H), 2.88-2.69 (m, 4H), 2.45 (s, 3H), 2.04 (m, 4H), 1.72-1.60 (m, 2H), 1.43-1.13 (m, 10H), 0.89 (t, J=6.9 Hz, 3H).

Second, sodium hydride (6.0 mg, 0.24 mmol) was added to a solution of 5-mercapto-2,4-dihydro-3H-1,2,4-triazol-3-one (28 mg, 0.24 mmol) in DMF (1 ml). Vigorous gas evolution was observed. After 5 min, a solution of the (6Z,9Z,12Z)-octadeca-6,9,12-trien-1-yl 4-methylbenzenesulfonate (66 mg, 0.16 mmol) in DMF (1 ml) was added dropwise. After 1 h, the reaction was poured into dichloromethane, acidified with 1N HCl and washed with water and brine. The organic layer was dried over magnesium sulfate, filtered and concentrated. The crude residue was purified by column chromatography eluting with 0-5% methanol in dichloromethane to give the desired prodrug as a white solid (45 mg, 79%). MS (ESI) m/z 362.23 (M-H); $^1$H NMR (500 MHz, DMSO-$d_6$) δ ppm 11.60 (s, 1H), 11.46 (s, 1H), 5.46-5.10 (m, 6H), 2.93 (t, J=7.3 Hz, 2H), 2.76 (t, J=5.8 Hz, 4H), 2.01 (m, 4H), 1.57 (m, 2H), 1.43-1.14 (m, 10H), 0.84 (t, J=6.8 Hz, 3H).

Preparation of Washed Murine Platelets.

The 12-LOX null C57BL/6 (12-LOX$^{-/-}$) mice were generated using homozygous breeding pairs and wild-type (WT) C57BL/6 (12-LOX$^{+/\pm}$) mice were purchased (Jackson Laboratory). Blood was drawn from the inferior vena cava of anesthetized 8-12 week old mice with a 21-gauge needle attached to a 1 mL syringe containing 100 μl of 3.8% sodium citrate. Mouse blood was diluted with equal volumes of Tyrode's buffer (10 mM HEPES, 11.9 mM sodium bicarbonate, 127.2 mM sodium chloride, 5 mM potassium chloride, 0.4 mM sodium phosphate monobasic, 1 mM magnesium chloride, and 5 mM D-glucose) and centrifuged at 200×g. Platelet-rich-plasma (PRP) was transferred to a tube containing 10× acid citrate dextrose solution (ACD) (2.5% sodium citrate, 1.5% citric acid, and 2% D-glucose) and apyrase (0.02 U/mL), and centrifuged at 2000×g. Platelet count was adjusted to 3×10$^8$ platelets/mL with Tyrode's buffer for all studies.

Preparation of Washed Human Platelets.

Blood from healthy donors was collected into vacutainers containing buffered sodium citrate, and platelets were isolated by serial centrifugation as described above for mouse platelets. The platelets were resuspended in Tyrode's buffer at 3×10$^8$ platelets/mL, unless otherwise specified.

Extraction, Liquid Chromatography, and Mass Spectrometry (LC/MS) Quantification of Oxylipins.

Washed human platelets were treated with agonists in the presence of vehicle control or specific fatty acids were frozen and then thawed to be acidified with 40 μL of 1M hydrochloric acid to an approximate pH of 3. Extraction standards were then added to the samples: 20 ng each of PGE$_1$-$d_4$ and 13(S)HODE-$d_4$. Oxylipids were extracted thrice with 2 mL of dichloromethane (6 mL total), reduced with about 100 μL trimethylphosphite, and dried under a stream of nitrogen gas. The samples were then reconstituted in 50 μL of methanol containing 10 ng of each of the internal standards, TxB$_2$-$d_4$, PGE$_2$-$d_4$, and 12(S)HETE-$d_8$, and transferred to MS vials with inserts.

Chromatographic separation was performed on a Dionex UltiMate 3000 UHPLC with a $C_{18}$ column (Phenomenex Kinetex, 1.7 μm, 150 mm×2.1 mm). The autosampler was held at 4° C. and injection volume was 30 μL. Mobile phase A consisted of water with 0.1% (v/v) formic acid and mobile phase B was acetonitrile with 0.1% formic acid. Flow rate was 0.400 mL/min. The initial condition (30% B) was maintained for 2.33 minutes. Mobile phase B was then ramped to 65% over 28.67 minutes, held at 65% for 1 minute, ramped to 100% over 0.1 min, held at 100% for 7 minutes, and finally returned to 30% to equilibrate for 7 minutes. The chromatography system was coupled to a Velos Pro linear ion trap (Thermo Scientific) for mass analysis. Analytes were ionized via heated electrospray ionization with −4.0 kV spray voltage, 60, 10, and 0 arbitrary units for sheath, auxiliary, and sweep gas, respectively. The RF amplitude of the S-Lens was 49%, and the probe and capillary temperatures were 50° C. and 380° C., respectively. All analyses were performed in negative ionization mode at normal resolution setting. MS$^2$ was performed in both a data dependent manner and a targeted manner, simultaneously from ions detected in a full scan with a mass-to-charge ratio (m/z) range of 200-400. The data dependent MS$^2$ were selected for the most intense eluting ion, while the targeted MS$^2$ were selected for the parent ions of the analytes that were contained in a mass list -TxB$_1$ (m/z=371.2), TxB$_2$ (m/z=369.2), TxB$_2$-$d_4$ (m/z=373.3), PGE$_1$ (m/z=353.2), PGE$_2$ (m/z=351.2), PGE$_1$-$d_4$ (m/z=357.2), PGE$_2$-$d_4$ (m/z=355.2), 12HETE (m/z=319.2), 12(S)HETrE (m/z=321.2), 12(S)HETE-$d_8$ (m/z=327.3), 13(S)HODE-$d_4$ (m/z=299.3).

Mass Spectrometry Analysis, Normalization, and Relative Quantitation of Oxylipins. Retention times and fragmentation patterns of all analytes were determined with lipid standards prior to sample analyses. Deuterated standards spiked into the platelet samples demonstrated no matrix-dependent shifts in retention times. Total ion counts (TIC) of the m/z transitions of each analyte peak were used for relative quantitation. The m/z transitions of all analytes and standards were as follows: $TxB_1$ (m/z=371.2→197), $TxB_2$ (m/z=369.2→195), $TxB_2\text{-}d_4$ (m/z=373.3→199), $PGE_1$ (m/z=353.2→317), $PGE_2$ (m/z=351.2→315), $PGE_1\text{-}d_4$ (m/z=357.24321), $PGE_2\text{-}d_4$ (m/z=355.2→319), 12HETE (m/z=319.2→179), 12HETrE (m/z=321.2→181), 12(S)HETE-$d_8$ (m/z=327.3→184), and 13(S)HODE-$d_4$ (m/z=299.3→198). Nanograms of 12-HETE and 12-HETrE present in sample were estimated based on TICs of 12-HETE and 12-HETrE relative to the TIC of 10 ng of 12-HETE-$d_8$. These nanogram estimates were then corrected for extraction efficiency by the percent recovery of 13-HODE-$d_4$ in each sample. The TIC of $TxB_1$, $TxB_2$, $PGE_1$, and $PGE_2$ were normalized to $PGE_1\text{-}d_4$ for extraction. For ionization, $TxB_1$ and $TxB_2$ were normalized to $TxB_2\text{-}d_4$, and $PGE_1$ and $PGE_2$ were normalized to $PGE_2\text{-}d_4$.

Platelet Aggregation.

A lumi-aggregometer (Chrono-log model 700D) was used to measure platelet aggregation under stirring conditions (1100 rpm) at 37° C. Prior to agonist stimulation platelets were incubated with a preselected PUFA or oxylipin for 10 minutes.

Rap1 Activation.

Washed platelets were incubated with a PUFA or oxylipins for 10 minutes prior to stimulation with 200 µM of PAR4-AP. Following 1 minute of stimulation platelets were lysed with 2× platelet lysis buffer (100 mM Tris HCl, pH 7.4, 150 mM NaCl, 2% IGEPAL, 1% sodium deoxycholate, and 0.05% SDS) containing protease and phosphatase inhibitors. The cytoskeleton was pelleted by centrifugation at 14000×g for 7 minutes at 4° C. Active Rap1 was selectively captured from the supernatant by incubating GST-tagged Rap1 binding domain of RalGDS conjugated to glutathione sepharose beads for one hour on a nutator at 4° C. The beads were then washed 5 times with IP buffer and resuspended in 2× Laemmeli reducing buffer (62.5 mM Tris-HCl, pH 6.8, 2% SDS, 25% glycerol, 0.01% bromophenol blue, 5% β-mercaptoethanol). The samples were boiled for 10 minutes and then loaded onto a 10% SDS-polyacrylamide gel electrophoresis (PAGE) gel. Western blots were performed using a Rap1 antibody and quantified with a LI-COR imager.

Laser-Induced Cremaster Arteriole Thrombosis Model.

Wild type (WT) or 12-LOX$^{-/-}$ mice (12 weeks of age) were anesthetized by intraperitoneal injection of ketamine/xylazine (100 mg/kg) prior to the exposure of the cremaster muscle arterioles under a dissecting microscope with constant perfusion of preheated bicarbonate-buffered saline (Reheman et al., J Thromb Haemost 3:875-883, 2005; Reheman et al., Blood 113:1809-1817, 2009; Wang et al., J Clin Invest 124:4281-4293, 2014). Anti-platelet (DyLight 488 anti-GPIb, 1 µg/g) and anti-fibrin (Alexa Fluor 647, 0.3 µg/g) antibodies were administered via jugular vein catheter prior to intravital microscopy. DGLA (50 mg/kg) or DMSO (vehicle control) were dissolved in a formulation of 5% DMSO and 45% PEG300 in sterile 1×PBS and then intravenously injected into mice 10 minutes prior to induction of thrombosis. 12(S)-HETrE (6 mg/kg) or equal volume of DMSO (vehicle control) was also intravenously injected into mice 10 minutes prior to induction of thrombosis. Multiple independent thrombi were induced in the arterioles (30-50 µm diameter) in each mouse by a laser ablation system (Ablate! photoablation system; Intelligent Imaging Innovations, Denver, Colo., USA). Images of thrombus formation were acquired in real-time under 63× water-immersion objective with a Zeiss Axio Examiner Z1 fluorescent microscope equipped with solid laser launch system (LaserStack; Intelligent Imaging Innovations) and high-speed sCMOS camera. All captured images were analyzed on Slidebook (Intelligent Imaging Innovations Inc., Denver, Colo., USA).

Tail Bleeding Assay.

Mice were anesthetized with ketamine/xyzaline and placed on a heating pad in prone position, the tip of the tail (5 mm) was excised with a sterile scalpel, and the tails were immediately immersed into isotonic saline solution (0.9%) warmed to 37° C. Bleeding time was assessed until cessation of blood flow from the tail for 1 minute.

Cremaster Muscle Arterial Puncture Model of Hemostasis.

Mice were anesthetized, tail vein injected with anti-platelet and anti-fibrin antibodies and their cremaster muscle arterioles were prepared as described above. A high intensity laser pulse from the laser ablation system was used to puncture a hole in the cremaster muscle arteriole wall as visualized by red blood cell (RBC) leakage from the vessel. Images of RBCs leakage and hemostatic plug formation were acquired in real-time with a fluorescent microscope as described above. Arterial bleeding time was defined as the time from laser pulse injury until cessation of RBC leakage from the vessel.

Liquid Chromatography Extraction and Mass Spectrometry (LC/MS) Quantification of cAMP.

Washed human platelets were treated with the specific ligand or vehicle control for 1 min at room temperature, and quenched with an equal volume of ice-cold 2× platelet lysis buffer containing protease and phosphatase inhibitors. Lysed platelet samples were centrifuged at 14,000 g for 7 min at 4° C. to pellet cytoskeleton and the supernatant was stored in −80° C.

To prepare the sample for LC/MS injection, 200 µL of the supernatant was spiked with 400 pg of adenosine-3',5'-cyclic-13C5 monophosphate ($^{13}C_5$-cAMP) (Toronto Research Chemicals, Inc.), an internal standard, and 600 µL of LC/MS grade acetonitrile (Fisher Scientific). The sample was briefly vortexed and centrifuged at 14,000 rpm for 10 min at 4° C. The supernatants were then air dried in a SpeedVac and reconstituted in 200 µL of LC/MS grade water and centrifuged at 10,000 rpm for 5 min at 4° C. and used for LC/MS injection.

The separation and detection of cAMP was performed on a Waters ACQUITY UPLC system equipped with a Xevo Triple Quadrupole Mass Spectrometer (TQ-S MS/MS).

The extraction/purification of cAMP from the sample was carried out using a Waters HSS C18 column (1.8 µm, 2.1*100 mm) that had been equilibrated for 1 min in 0.1% formic acid in water (solvent A) with a constant flow rate of 0.5 mL/min. The sample (10 µL) was then injected. The column was washed for 4 minutes with solvent A and then gradually flushed with 10% of 0.1% formic acid in acetonitrile (solvent B) to remove nonspecific interactions from the column. The column was eluted with 70% of solvent A at 5 min, which then decreased to 1% at 7 min.

The mass spectrometer was operated with an ESI source in positive mode. The electrospray voltage was 3.9 kv. The source temperature was maintained at 150° C., and the desolvation temperature was 525° C. with a nitrogen desolvation gas flow of 1000 L/h. Cyclic AMP (cAMP) was quantitated using $^{13}C_5$-cAMP as the internal standard. For cAMP monitoring in the MRM mode with a collision energy of 22 volts, 330/136 mass transition was used, and for $^{13}C_5$-cAMP, 335/136 was used.

VASP Phosphorylation in Human Platelets.

Washed platelets were treated with PUFA or PUFA metabolite (12(S)-HETrE or compound IIc) for one minute, then directly lysed in 5× Laemmeli sample buffer (1.5 M Tris-HCl, pH 6.8, glycerol, 5% β-mercaptoethanol, 10% sodium dodecyl sulfate (SDS), and 1% bromophenol blue). The samples were boiled for five minutes and then run on a 10% SDS-PAGE gel. The levels of total and phospho-VASP (serine 157) were quantified by Western Blot using an Odyssey imaging system (LI-CoR).

Membrane Preparation and [$^{35}$S]GTP γS Binding.

PRP was isolated from whole blood as described above and then incubated with 1 mM aspirin for 1 hour at 37° C. Platelets were pelleted at 2000 g for 10 min in the presence of 10×ACD and apyrase. The pelleted platelets were washed with Tyrode's and centrifuged at 2000×g with 10×ACD for 10 min at room temperature. The platelets were flash frozen with liquid nitrogen and then resuspended in cold detergent-free TME buffer (50 mM Tris-HCl, pH 7.5, 20 mM MgCl$_2$, 2 mM EDTA, and 100 mM NaCl) with 1 μM GDP and protease and phosphatase inhibitors to lyse the platelets. The lysed platelets were centrifuged at 1500 g at 4° C. for 5 min. The supernatant was collected and centrifuged at 100,000×g for 30 min at 4° C. The pelleted membranes were resuspended in TME buffer with 1 μM GDP and stored at −80° C. prior to use. Fatty acid metabolites, agonists, or DMSO and [$^{35}$S]GTPγS (10 nM) were added to platelet membranes (60 μg/reaction) on ice, and the tubes were immediately transferred to a 30° C. water bath shaker for 20 min. The reaction was terminated by the addition of ice-cold IP buffer (50 mM Tris-HCl, pH 7.5, 20 mM MgCl$_2$, 150 mM NaCl, 0.5% Nonidet P-40, 0.33% aprotinin, 0.1 mM GDP, and 0.1 mM GTP). The samples were pre-cleared with Protein A agarose beads and normal rabbit IgG for 30 min on a nutator at 4° C. and then aliquoted equally into two tubes containing either normal rabbit IgG or a G$_s$ antibody that had been conjugated to Protein A agarose beads. The samples were incubated on a nutator for 1 hr at 4° C. and washed 4 times with IP buffer and 1 time in TME buffer. The samples were boiled in 0.5% SDS for 30 sec, and the supernatants were collected following brief centrifugation. The supernatants were analyzed in 8 mL of scintillation fluid. The background counts for the normal rabbit IgG (50-200 cpm) for each sample were subtracted from the anti-G$_s$ immunoprecipitated samples prior to analyzing the data.

Animal Model of ITP.

Mice expressing the human immune-receptor FcγRIIa were injected IV with GPIX, an antibody known to induce acute ITP (Stolla et al., *Blood* 118(4): 1113-1120, 2011) as previously described (Yeung et al., *Blood* 124(4): 2271-2279, 2014). GPIX antibody injection has previously been shown to induce acute thrombocytopenia accompanied by accumulation of thrombi in the lungs. To determine if 12(S)-HETrE compounds would be viable therapeutics to prevent ITP in this model, 6 mg/kg 12(S)-HETrE was injected IV 10 minutes prior to GPIX antibody injection, and platelet count was measured at several time points prior to and following antibody injection. Additionally, immunofluorescent-labelled platelets that had been injected prior to the onset of ITP were measured in excised lungs 4 hours following GPIX administration. Treatment with 12(S)-HETrE prevented accumulation of fluorescently labeled platelets in the lungs, in contrast to treatment with the vehicle control.

To further assess prevention and potential resolution of ITP, 12(S)-HETrE compounds will be administered IV following ITP induction with anti-GPIX antibody. Platelet counts and CBC will be taken just prior to IV administration of anti-GPIX and again 4 hours post anti-GPIX administration. Following the second blood draw for platelet counts, the 12(S)-HETrE compounds will be administered IV, and after 30 minutes, a platelet count will be taken. Platelet counts will continue to be taken every 4 hours after the initial platelet count to assess recovery from thrombocytopenia and/or prevention of further platelet loss. Two days post-OxyProtect administration, the lungs and spleen will be excised, and the platelet accumulation and thrombus formation will be quantitatively assessed to confirm recovery of platelet count and resolution of pre-formed platelet thrombi.

Statistics.

Unpaired, paired two-tailed student t-tests, and two-way analysis of variance (ANOVA) were used to compare between experimental groups with Prism 6.0 software (GraphPad). Where appropriate the statistical test used is contained in the brief description of the figures. Data represents mean values+/−SEM.

Results

DGLA Inhibits Platelet Aggregation and Thrombus Growth in a 12-LOX Dependent Manner.

Figure 1B:
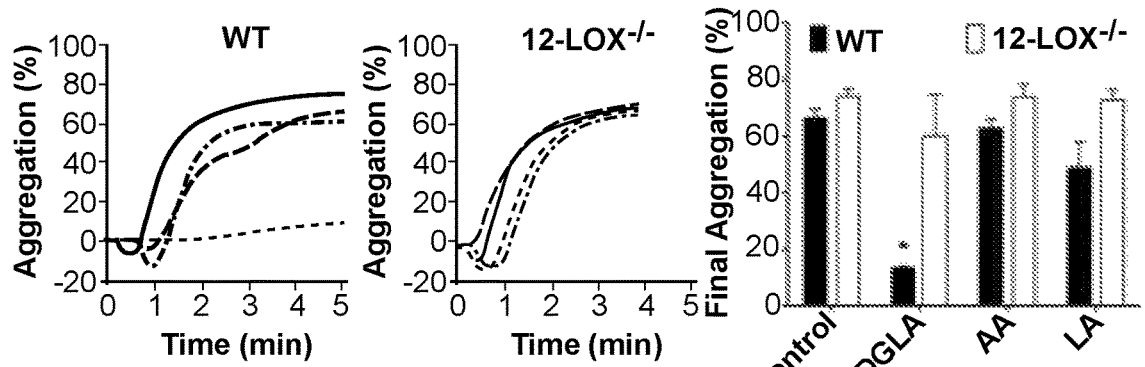

To assess the role of 12-LOX in DGLA-mediated platelet inhibition, washed platelets from WT or 12-LOX$^{-/-}$ mice were stimulated with an EC$_{80}$ concentration of either protease-activated receptor-4-activating peptide (PAR4-AP) or collagen in the presence or absence of DGLA. As previously reported, platelets from 12-LOX$^{-/-}$ mice were hypoactive compared to platelets from WT mice (Yeung et al., *Thromb Haemost* 110:569-581, 2013), hence, requiring a higher concentration of agonist to reach EC$_{80}$. Pretreatment of platelets from WT mice with DGLA resulted in significant inhibition of aggregation compared to DMSO treated platelets in response to PAR4-AP or collagen stimulation (FIG. 1A and FIG. 1B). Conversely, DGLA treatment of platelets from 12-LOX$^{-/-}$ mice failed to inhibit platelet aggregation in response to PAR4-AP or collagen stimulation (FIG. 1A and FIG. 1B). As the observed DGLA-mediated inhibition of aggregation may be due to the modification of the lipid membrane structure thus affecting platelet signaling or activation, other PUFAs including linoleic acid (LA) and AA were used as controls to rule out a lipid-membrane insulating effect in platelet activation (Simons and Toomre, *Blood* 123:e37-45, 2000). Pretreatment of platelets with either LA or AA had no inhibitory effect on PAR4-AP or collagen-mediated platelet aggregation compared to vehicle alone (FIG. 1A and FIG. 1B).

Figure 1C:
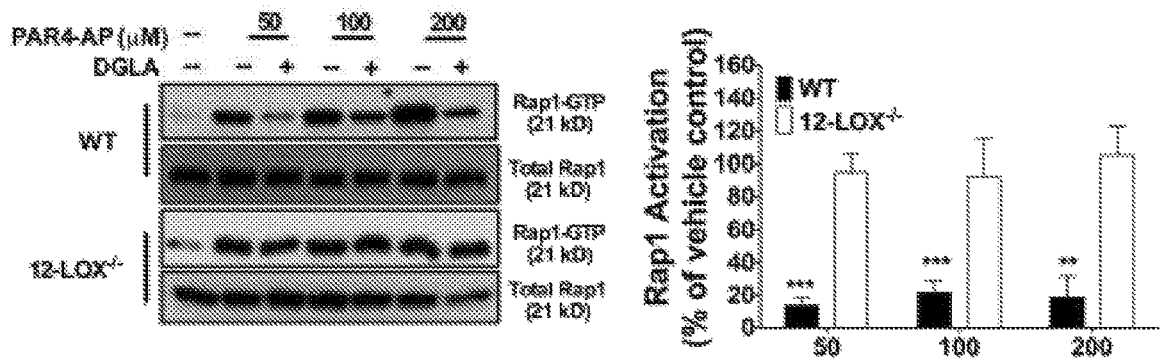

To determine if DGLA inhibited platelet aggregation by impinging on intracellular signaling, the activation of Rap1, a common signaling effector required for integrin α$_{IIb}$β$_3$ activation (Shattil et al., *Nat Rev Mol Cell Biol* 11:288-300, 2010; Shattil and Newman, *Blood* 104:1606-1615, 2004) was assessed in DGLA treated platelets stimulated with PAR4-AP Yeung et al., *Thromb Haemost* 110:569-581, 2014). In platelets isolated from WT mice, DGLA inhibited Rap1 activation at all concentrations of PAR4-AP tested (FIG. 1C). Since DGLA was unable to inhibit platelet aggregation in 12-LOX$^{-/-}$ mice, whether 12-LOX was also necessary for DGLA inhibition of Rap1 activation in platelets was assessed. Consistent with the platelet aggregation data, DGLA was unable to inhibit Rap1 activation in platelets from 12-LOX$^{-/-}$ mice at any of the concentrations of PAR4-AP tested (FIG. 1C). Together, these data demonstrate that the antiplatelet effects mediated by DGLA require 12-LOX.

Figure 1D:
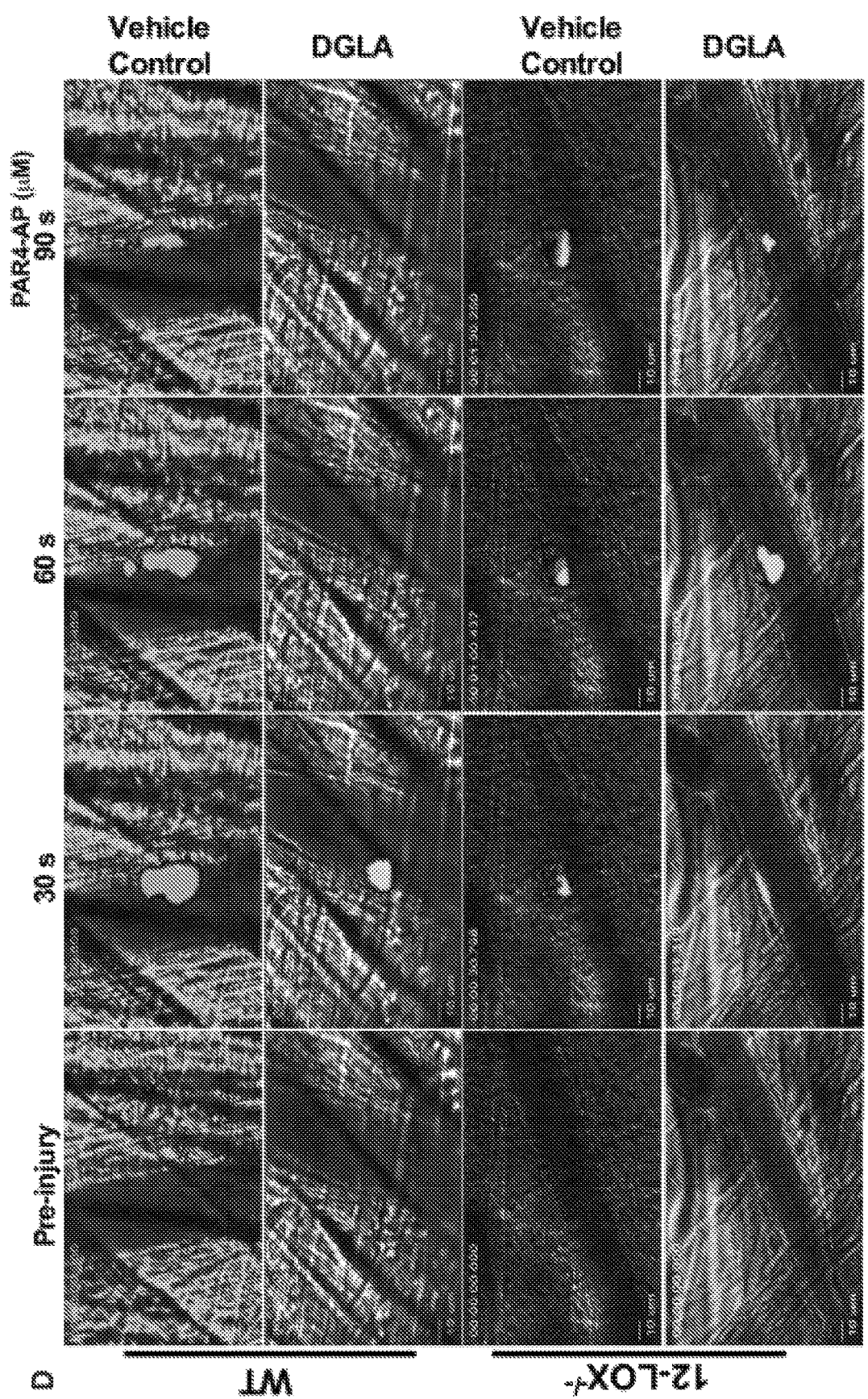
Figure 1E:
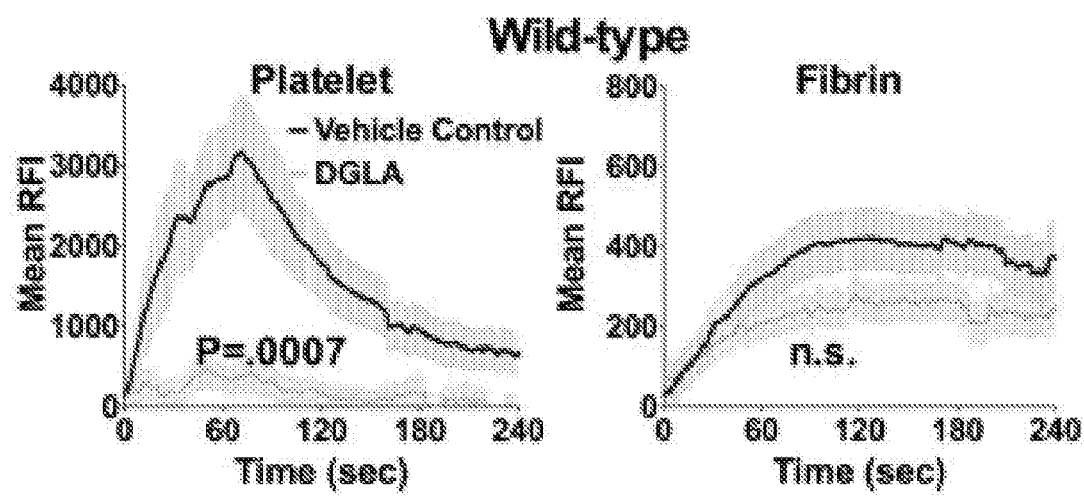
Figure 1F:
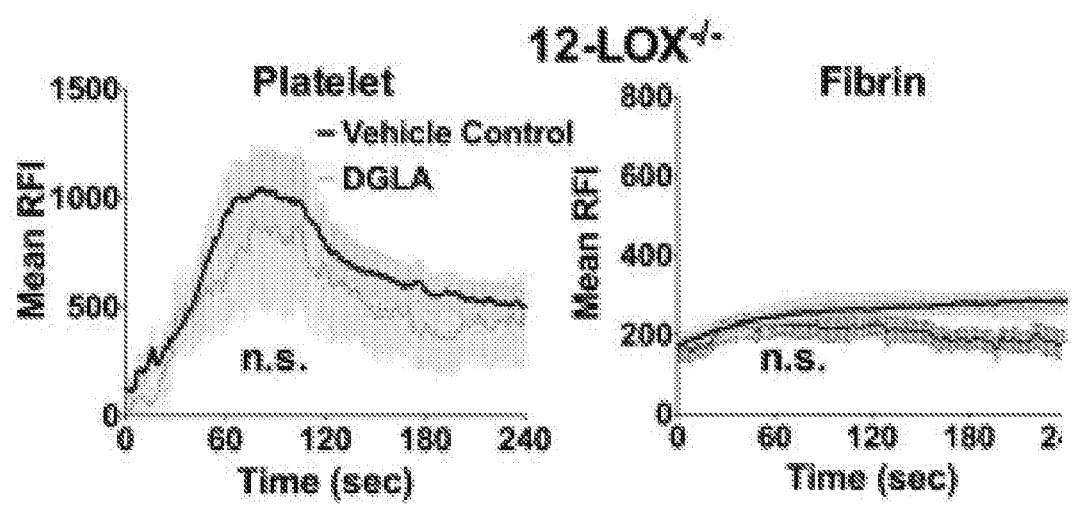

To determine whether the antiplatelet effects of DGLA observed ex vivo could contribute to the inhibition of platelet thrombus formation in vivo, a laser-induced cremaster arteriole thrombosis model was employed to examine thrombus formation (platelet and fibrin) in WT mice (Falati et al., *Nat Med* 8:1175-1181, 2002) (FIG. 1D-FIG. 1F). Mice were intravenously injected with either vehicle control (DMSO) or 50 mg/kg of DGLA 10 minutes prior to the initiation of thrombosis by laser injury. Following vessel injury of vehicle control treated WT mice, fluorescently labeled platelets rapidly accumulated at the site of vascular injury then drastically diminished in size as the clot was resolved (FIG. 1D and FIG. 1E). Simultaneously, fibrin formation can be seen at the base of the developing thrombus of vehicle control treated WT mice (FIG. 1D and FIG. 1E). WT mice treated with DGLA showed a significant reduction in platelet, but not fibrin accumulation (FIG. 1D and FIG. 1E).

FIG. 1A-FIG. 1C support a requirement for 12-LOX in DGLA-mediated platelet activation ex vivo. To determine if this observation translates to an attenuation of platelet reactivity in vivo, thrombus formation was measured in 12-LOX$^{-/-}$ mice following laser injury (FIGS. 1, D and F). As previously reported, platelets from 12-LOX$^{-/-}$ mice exhibited a bleeding diathesis compared to WT mice as determined by the tail-bleeding assay (Yeung et al., supra). Therefore, it would be expected that the 12-LOX$^{-/-}$ mice show a significant attenuation of thrombus following injury compared to the WT (FIG. 1D and FIG. 1F). Interestingly, the accumulation of platelet and fibrin in thrombi between DGLA-treated 12-LOX$^{-/-}$ and vehicle control did not differ (FIG. 1D and FIG. 1F). The in vivo data confirmed the ex vivo observation that 12-LOX is required to mediate the inhibition of platelet function, as well as thrombosis.

The Derived Oxylipin of 12-LOX, 12(S)-HETrE, Inhibits Platelet Aggregation and Thrombus Growth.

Figure 2A:
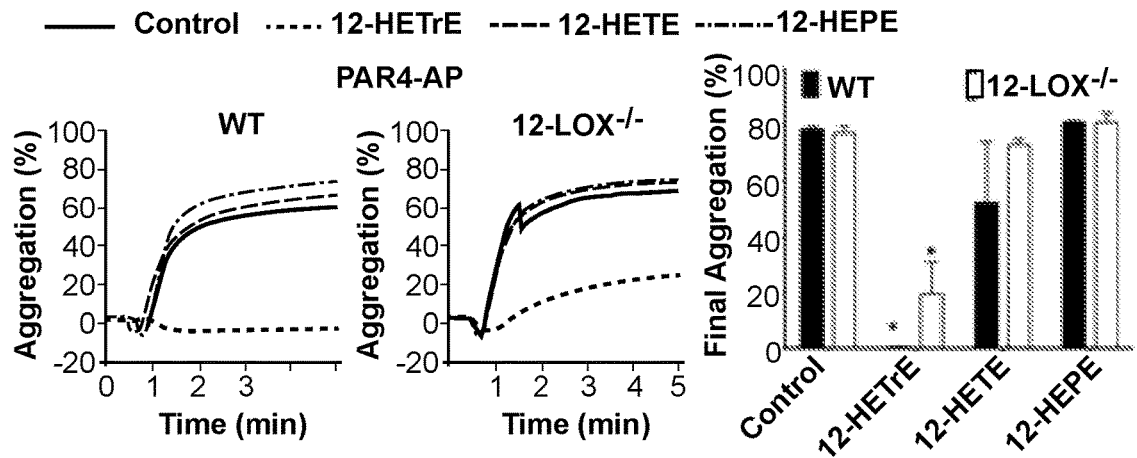
FIGS. 2A to 2E show that 12(S)-HETrE inhibits platelet aggregation and thrombus formation. Representative tracings and combined aggregation data of washed platelets from (FIG. 2A) WT (n=4) or (FIG. 2B) 12-LOX$^{-/-}$ (n=4) mice pre-treated with 25 µM 12-LOX oxylipins (12-HETrE, 12-HETE, or 12-HEPE) for 10 minutes prior to stimulation with an $EC_{80}$ concentration of PAR4-AP (WT 100 µM; 12-LOX$^{-/-}$ 200 µM) or collagen (WT 5 µg/mL; 12-LOX$^{-/-}$ 2 or 5 µg/mL) in an aggregometer. Data represents mean±SEM. *P<0.05 two-tailed unpaired t-test.
Figure 2B:
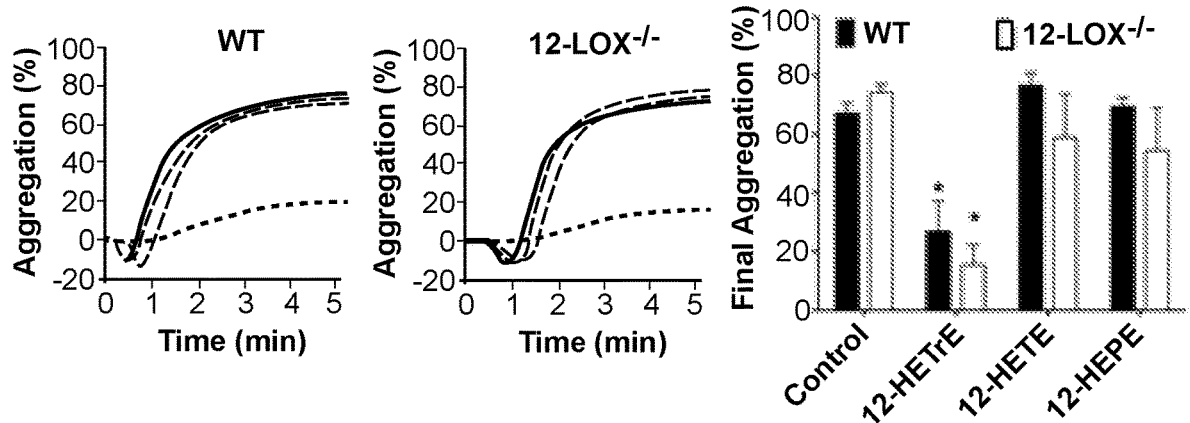

To confirm that 12(S)-HETrE was the 12-LOX product of DGLA mediating the inhibitory effects observed in FIG. 1A-FIG. 1F, washed platelets from either WT or 12-LOX$^{-/-}$ mice were treated with 12(S)-HETrE followed by stimulation with either PAR4-AP or collagen. Notably, 12(S)-HETrE (25 μM) inhibited the aggregation of platelets from WT and 12-LOX$^{-/-}$ mice similarly in response to PAR4-AP or collagen (FIG. 2A and FIG. 2B). As expected, no decrease in collagen- or PAR4-AP-mediated platelet aggregation was observed in either WT or 12-LOX$^{-/-}$ platelets pre-treated with 12-HETE, the pro-thrombotic 12-LOX-derived oxylipin of AA, compared to vehicle control. Additionally, incubation of platelets with 12-HEPE, a 12-LOX-derived oxylipin of eicosapentaenoic acid (EPA) with no known effects on aggregation (de Oliveira Otto et al., *J Am Heart Assoc* 2:e000506, 2013; Dyerberg et al., *Lancet* 2:117-119, 1978; Ikei et al., supra), did not inhibit collagen- or PAR4-AP-induced aggregation in platelets from either WT or 12-LOX$^{-/-}$ mice.

Figure 2C:
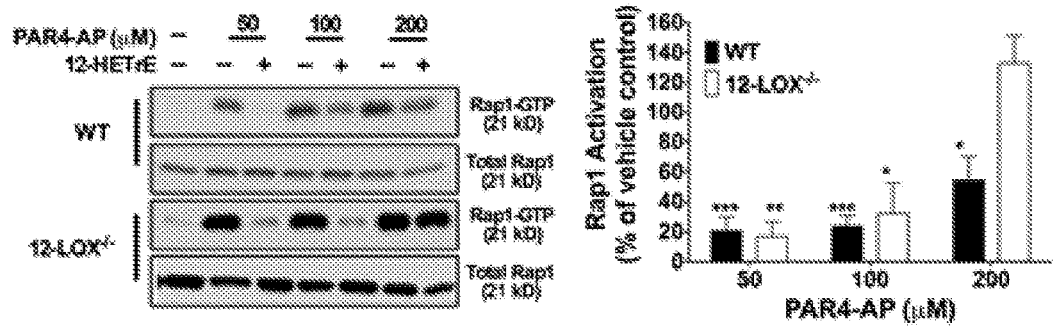

To determine if 12(S)-HETrE inhibits intracellular signaling, the activation of Rap1 was measured in PAR4-AP stimulated platelets in the presence of 12(S)-HETrE or vehicle control. 12(S)-HETrE suppressed Rap1 activation compared to vehicle control in platelets from either WT or 12-LOX$^{-/-}$ mice (FIG. 2C). Thus, 12(S)-HETrE was able to inhibit platelet aggregation and Rap1 activity independent of 12-LOX expression.

Figure 2D:
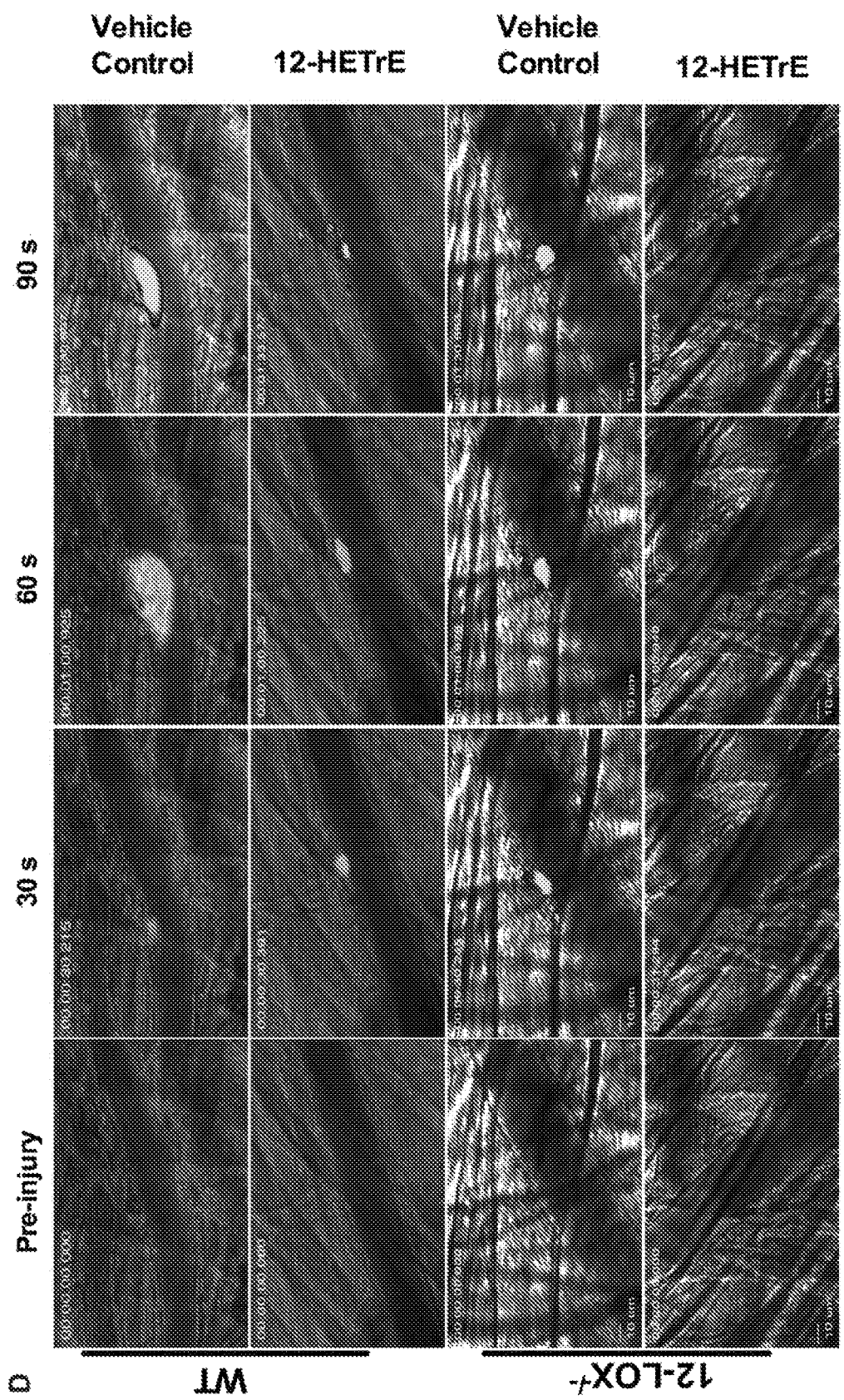
Figure 2E:
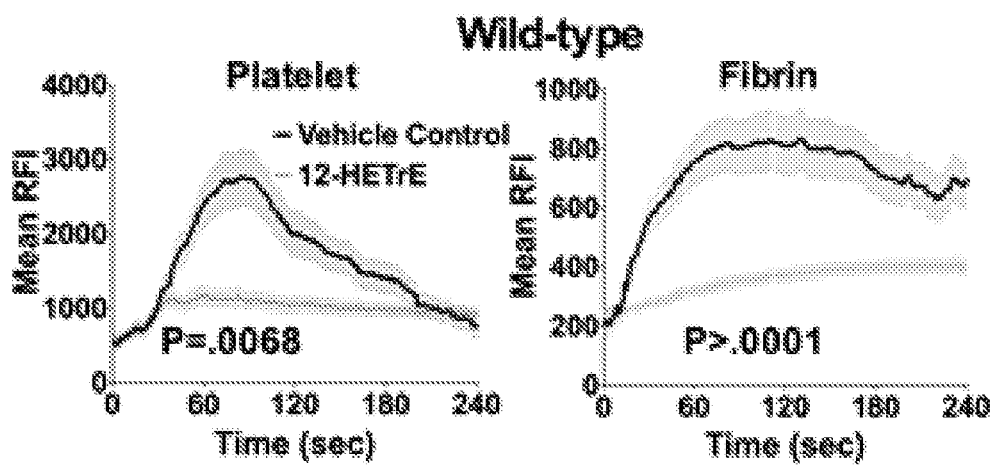
Figure 2F:
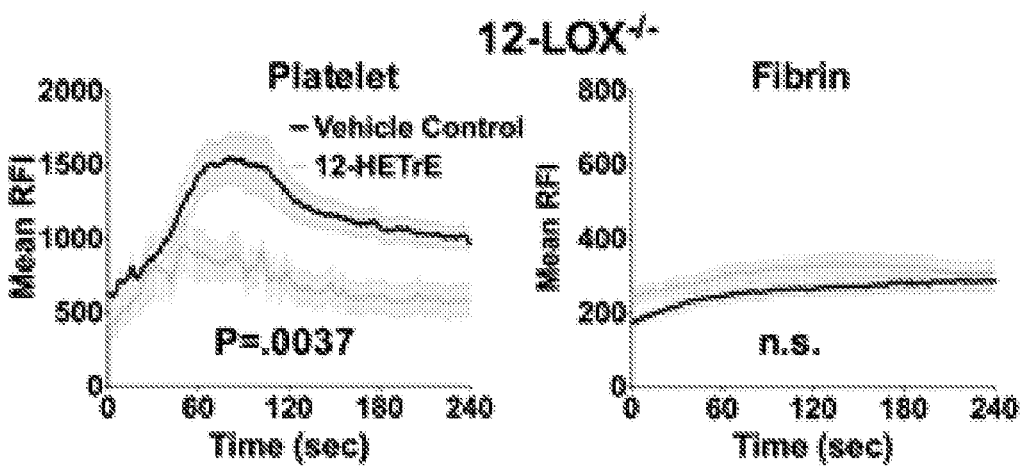

Although 12(S)-HETrE significantly attenuated platelet activation, it remained unclear if 12(S)-HETrE could inhibit platelet thrombus formation in vivo. To evaluate the effects of 12(S)-HETrE on thrombus formation, the size and kinetics of the growing arterial thrombus were assessed following laser-induced injury of the cremaster muscle arterioles in WT and 12-LOX$^{-/-}$ treated with vehicle control or 6 mg/kg of 12(S)-HETrE (FIG. 1D and FIG. 2D). Following injury, platelets and fibrin were observed to rapidly accumulate at the injured arteriole wall in WT control mice (FIG. 2D). In contrast, WT mice treated with 12(S)-HETrE had significantly smaller and less stable thrombi in response to laser injury as assessed by both platelet and fibrin accumulation (FIG. 2D and FIG. 2E). 12-LOX$^{-/-}$ mice treated with vehicle control had already exhibited significant decrease in thrombus formation, i.e., platelet and fibrin accumulation (FIG. 2D and FIG. 2F) compared to WT control following injury (FIG. 2D and FIG. 2E). Additionally, 12-LOX$^{-/-}$ mice treated with 12(S)-HETrE exhibited significant inhibition of platelet accumulation compared to 12-LOX$^{-/-}$ alone (FIG. 2F). However, no difference in fibrin accumulation was observed between vehicle control and 12(S)-HETrE treatment of 12-LOX$^{-/-}$.

DGLA-Induced Oxylipin Production.

Endogenously, only minute amounts of DGLA metabolites are produced by COX-1 (PGE$_1$ and TxB$_1$) or 12-LOX (12-HETrE) due to the low abundance of DGLA in the platelet plasma membrane (Tourdot et al., *Front Pharmacol* 4:176, 2014). To determine if the exogenous addition of DGLA (10 μM) increases the production of 12-LOX and COX-1 metabolites, the lipid released from platelets stimulated with PAR4-AP in the presence of vehicle control or DGLA was measured by LC/MS/MS. As expected, the amount of DGLA-dependent COX-1 and 12-LOX oxylipins was significantly potentiated in the DGLA-treated group compared to the DMSO control group (FIG. 3A and FIG. 3B). The amount of AA-dependent metabolites from either 12-LOX (12-HETE) or COX-1 (TxB$_2$ or PGE$_2$) was unaltered in platelets incubated with DGLA (FIG. 3A and FIG. 3B) supporting 12-LOX being in excess such that competition for the substrate is not necessary.

12(S)-HETrE does not Disrupt Hemostasis.

Since 12(S)-HETrE potently attenuated platelet accumulation in the laser-induced cremaster injury model of thrombosis, it was considered possible that 12-HETrE alters hemostasis, resulting in increased bleeding. To determine if 12(S)-HETrE treatment results in an increased bleeding diathesis, two hemostatic models were used to assess the impact of 12(S)-HETrE on bleeding. First, the tail-bleeding time assay was utilized to determine the effects of 12(S)-HETrE on primary hemostasis. 12(S)-HETrE-treated mice showed no significant difference in tail bleeding time compared to the control mice following excision of the distal segment (5 mm) of the tail (FIG. 4A). To confirm this assay was accurately reporting bleeding risk, heparin-treated mice were also assayed for bleeding time and observed to have a severe bleeding diathesis (data not shown). A second hemostatic model was used to confirm hemostasis was not significantly altered following treatment with 12(S)-HETrE. This model involved arteriole puncture of the cremaster muscle induced by severe laser injury (Welsh et al., *Blood* 127:1598-1605, 2016) in order to monitor the cessation time of RBC leakage from the punctured arteriole wall (FIG. 4B). No significant difference in the duration of RBC leakage was observed between 12(S)-HETrE and control treated mice. In both the control and 12(S)-HETrE-treated mice, a stable, non-occlusive clot formed in response to laser puncture of the vessel wall, resulting in cessation of RBC leakage from the vessel (data not shown). Both distinct hemostatic models demonstrated that 12(S)-HETrE does not disrupt hemostasis.

12(S)-HETrE Inhibits Platelets in a Gα$_s$-Linked GPCR-Dependent Manner.

COX-derived oxylipins that inhibit platelet function primarily exert their inhibition through the activation of a GPCR coupled to Gα$_s$ resulting in adenylyl cyclase (AC) activation (Gorman et al., *Prostaglandins* 13:377-388, 1977; Tateson et al., *Prostaglandins* 13:389-397, 1977) and the generation of cAMP (Haslam, *Ciba Found Symp* 35:121-151, 1975; Haslam et al., *Adv Cyclic Nucleotide Res* 9:533-552, 1978a; Haslam et al., *Thromb Haemost* 40:232-240, 1978b; Miller and Gorman, *J Cyclic Nucleotide Res* 2:79-87, 1976; Noe et al., *Curr Med Chem* 17:2897-2905, 2010). To determine if DGLA-derived 12-LOX oxylipins could be regulating platelet reactivity in a similar manner, cAMP formation was measured in washed human platelets stimulated with 12(S)-HETrE or 12-HpETrE, a peroxidated, labile precursor of 12-HETrE. Following a 1 minute stimulation with 12(S)-HETrE or 12-HpETrE (Ikei et al., supra), human platelets exhibited a significant increase in the level of intracellular cAMP compared to vehicle treated (DMSO) platelets (FIG. 5A). As expected, platelets stimulated with forskolin, a direct activator of AC, also showed an increase in cAMP levels. 12-HETrE-induced cAMP production is suggestive of 12(S)-HETrE inhibiting platelets through the activation of AC. To assess if 12(S)-HETrE inhibits platelet aggregation in an AC dependent manner, platelets were pre-treated with SQ 22536, an AC inhibitor (Armstrong et al., *Br J Pharmacol* 87:543-551, 1986) prior to incubation with 12(S)-HETrE or iloprost, a prostacyclin receptor agonist known to signal through AC (Riva et al., *Am J Respir Cell Mol Biol* 3:301-309, 1990; Turcato and Clapp, *Br J Pharmacol* 126:845-847, 1999). Iloprost and 12(S)-HETrE were unable to inhibit PAR4-AP-mediated platelet aggregation in platelets pre-treated with SQ 22536 (FIG. 5B), supporting an AC-dependent mechanism of platelet inhibition by 12(S)-HETrE.

The cAMP activated kinase, protein kinase A (PKA), phosphorylates multiple proteins in platelets including vasodilator-stimulated phosphoprotein (VASP). Since serine 157 (S157) in VASP is a known PKA substrate (Butt et al., *J Biol Chem* 269:14509-14517, 1994), VASP phosphorylation was used as a surrogate readout for PKA activation. Washed human platelets treated with DGLA or its 12-LOX metabolites (12(S)-HETrE, or 12-HpETrE) for 1 minute had enhanced VASP phosphorylation compared to DMSO treated platelets (FIG. 5C). Platelets treated with compound IIc also exhibited dose-dependent phosphorylation of VASP. As expected, forskolin treated platelets also had an increase in VASP phosphorylation. The data demonstrates that the cAMP produced in platelets following exposure to 12(S)-HETrE compounds is capable of eliciting physiological effects.

The activation of a GPCR coupled to Gα$_s$ leads to the dissociation of GDP and the subsequent binding of GTP to Gα$_s$ initiating a well-established signaling cascade resulting in increases in cAMP levels through the activation of AC (Gilman, *The Journal of clinical investigation* 73:1-4, 1984; Smigel et al., *Advances in cyclic nucleotide and protein phosphorylation research* 17:1-18, 1984). Since 12(S)-HETrE was shown to induce cAMP formation and inhibit platelet activation in an AC-dependent manner, whether 12-HETrE could activate Gα$_s$ was determined. Activation of Gα$_s$ was assessed by measuring the incorporation of the radiolabeled, non-hydrolyzable analog, [$^{35}$S]GTPγS, to Gα$_s$, immunoprecipitated from isolated platelet membranes following treatment (Zhang et al., *Mol Pharmacol* 75:235-241, 2009) with vehicle control (DMSO), 12(S)-HETrE, 12-HpE-TrE, PAR4-AP, or iloprost. Treatment of platelet membranes with 12(S)-HETrE, 12-HpETrE, and iloprost elicited a significant increase in [$^{35}$S]GTPγS binding to immunoprecipitated Gα$_s$ compared to platelet membranes incubated with DMSO (FIG. 5D). Activation of PAR4, a receptor that is known to selectively activate G$_q$ and G$_{12/13}$, showed no [$^{35}$S]GTPγS binding confirming the selectivity for Gα$_s$ activation in the assay.

12(S)-HETrE Prevents Thrombocytopenia and Thrombosis in the Lungs.

Figure 7:
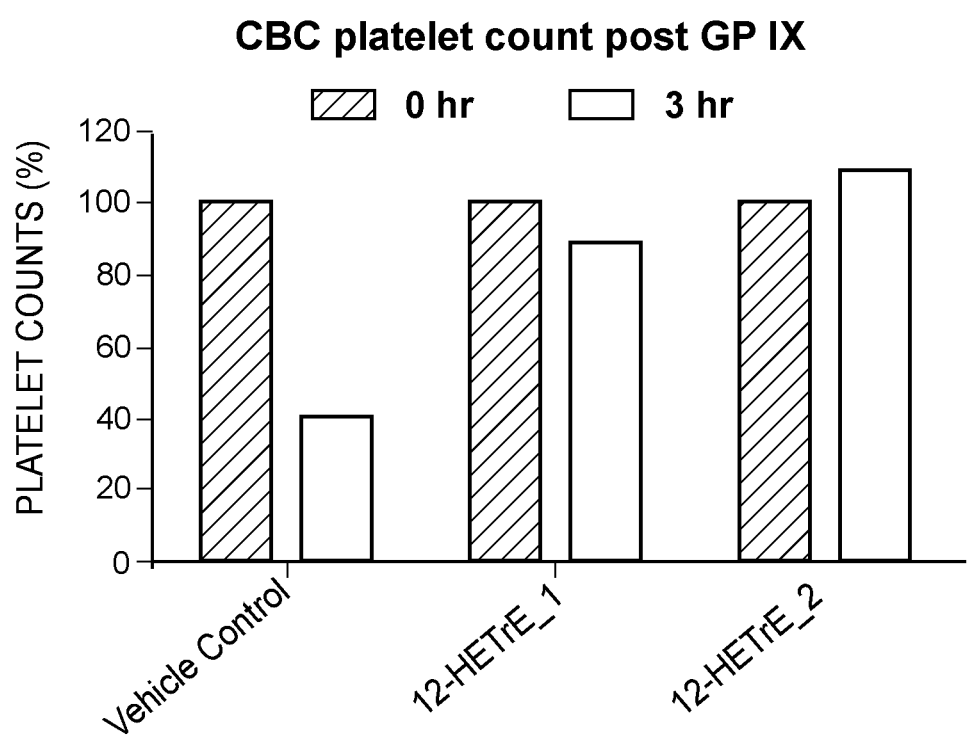
FIG. 7 shows 12(S)-HETrE treats thrombocytopenia in an animal model of ITP. Mice expressing the human FcγRIIa receptor on their platelets were treated with 12(S)-HETrE or vehicle control prior to administration of anti-GPIX to induce ITP. Treatment with 12(S)-HETrE prevented thrombocytopenia, i.e., a reduction in platelet counts, compared to treatment with the vehicle control.

To demonstrate that 12(S)-HETrE compounds are viable therapeutics to prevent ITP, 12(S)-HETrE was injected IV into mice 10 minutes prior to antibody injection (GPIX) to induce acute ITP, and platelet count was measured at several time points prior to and following antibody injection. Additionally, immunofluorescent-labelled platelets that had been injected prior to the onset of ITP, were measured in excised lungs following GPIX administration. The mice pre-treated with 12(S)-HETrE showed no signs of thrombocytopenia, i.e., a reduction in platelet count, and markedly reduced (more than 40% reduction) thrombi in the lungs (FIG. 7A and FIG. 7B).

Discussion

The relative contribution of 12-LOX-derived metabolites in DGLA-mediated inhibition of platelet function was studied. In contrast to the previously reported dependence of DGLA-mediated inhibition of platelet function on COX-derived metabolites, the Example shows that DGLA, but not 12(S)-HETrE, treatment of platelets from 12-LOX$^{-/-}$ mice was unable to inhibit platelet aggregation, suggesting that 12-LOX plays a key role in facilitating DGLA's antiplatelet effects.

The proposed inhibitory effect mediated through 12-LOX appears paradoxical based on previous work showing that 12-LOX is a positive mediator of platelet function (Nyby et al., *J Pharmacol Exp Ther* 278:503-509, 1996; Thomas et al., *J Biol Chem* 285:6891-6903, 2010; Yeung et al., *Thromb Haemost* 110:569-581, 2013; Yeung et al., *Blood* 124:2271-2279, 2014). However, due to the fact that 12-LOX is an enzyme whose function is to add an oxygen to a free fatty acid in order to produce a bioactive oxylipin, it is reasonable to conclude from the data and elsewhere (Falardeau et al., supra; Kernoff et al., *Br Med J* 2:1441-1444, 1977) that the substrate for 12-LOX is the determining factor in its effect on platelets and ultimately thrombosis. This conclusion is supported by work in COX which shows that oxidation of AA results in a pro-thrombotic milieu of oxylipins (Hamberg and Samuelsson, *Proceedings of the National Academy of Sciences of the United States of America* 71:3400-3404, 1974; Samuelsson, *J Biol Chem* 287:10070-10080, 2012), while other substrates such as DGLA can result in production of anti-thrombotic oxylipins (Farrow and Willis, supra; Levin et al., *Biochem J* 365:489-496, 2002; Willis et al., supra).

The potent inhibition of thrombus formation by both DGLA and 12(S)-HETrE, raises the potential that 12(S)-HETrE will cause excessive bleeding similar to other antiplatelet agents. Two hemostatic assays, the tail-bleeding assay and a second model, the laser-induced cremaster arteriole puncture model, were used to determine if the DGLA metabolite 12(S)-HETrE prolonged bleeding following vascular injury. Interestingly, 12(S)-HETrE did not significantly alter hemostasis in either assay, demonstrating that 12(S)-HETrE exerts an anti-thrombotic effect, while at the same time maintaining primary hemostasis.

Figure 6:
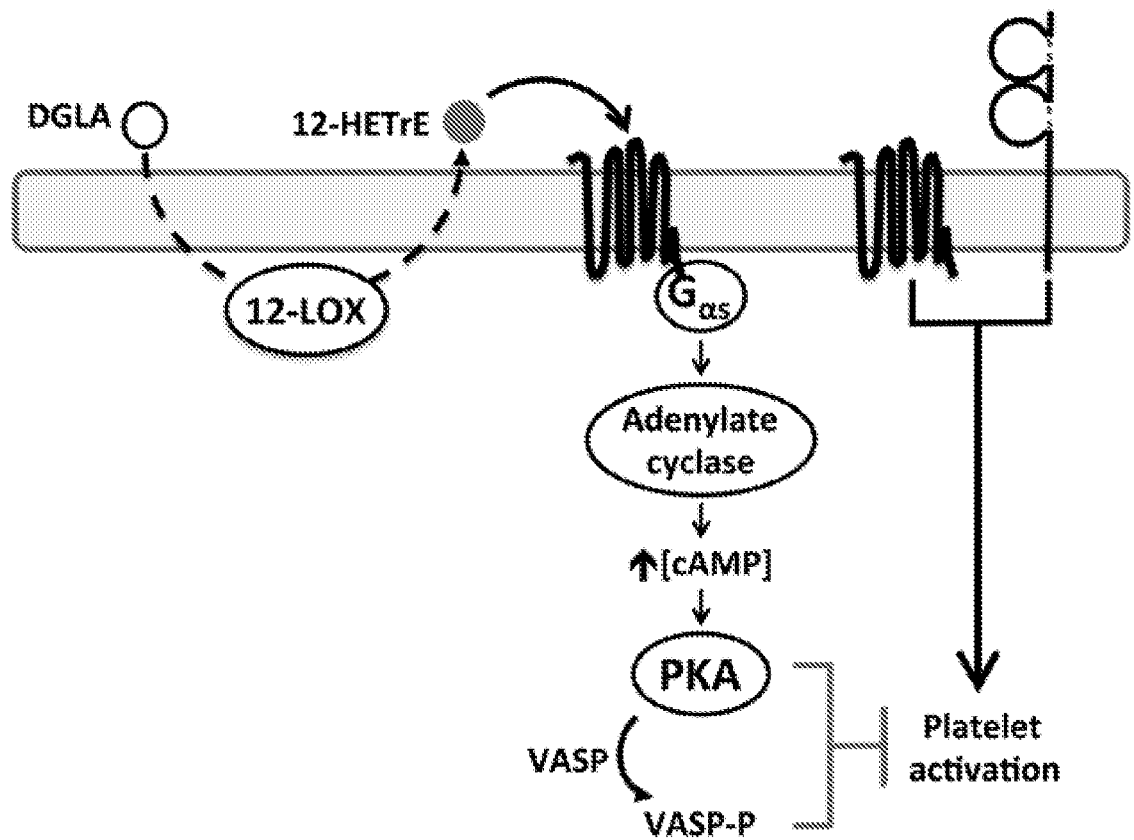
FIG. 6 shows a proposed model of 12(S)-HETrE inhibitory signaling in platelets. Within platelets, 12-lipoxygenase (12-LOX) metabolizes free DGLA into the bioactive lipid, 12-HETrE. 12-HETrE can passively diffuse through the plasma membrane and presumably bind to an unidentified Gα$_s$ coupled receptor in a paracrine or autocrine manner. Gα$_s$ activates adenylyl cyclase, which increases the intracellular level of cyclic AMP (cAMP). Elevated cAMP activates protein kinase A (PKA), which phosphorylates a number of proteins, including vasodilator-stimulated phosphoprotein (VASP), leading to platelet inhibition in response to either GPCR or ITAM mediated platelet activation.

12(S)-HETrE was found to directly activate a Gα$_s$-coupled GPCR. Direct addition of 12(S)-HETrE to purified platelet membranes was shown to increase the binding of [$^{35}$S]GTPγS, the hydrolysis-resistant GTP analog, to the Gα$_s$-subunit resulting in cAMP formation, activation of PKA, and phosphorylation of VASP (FIG. 6).

The foregoing Example supports the use of 12(S)-HETrE compounds (i.e., 12(S)-HETrE and compounds of Formulas (0), (I) and (II)) and compositions comprising the same as a viable approach for the prevention and treatment of thrombosis, thrombocytopenia, and thrombotic disorders. The discovery of 12(S)-HETrE regulation of platelet function at both the ex vivo and in vivo levels and the delineation of the mechanism of action through the Gα$_s$-coupled GPCR establishes these oxylipins as important eicosanoids in platelet biology. Beyond the platelet, 12(S)-HETrE could play an important role in the regulatory function of other vascular cells similar to what is observed with other key eicosanoids produced in the platelet, such as prostacyclin, PGE, PGD, and thromboxane. The 12(S)-HETrE compounds and compositions of the disclosure can be used to alter the platelet signalosome in order to attenuate unwanted platelet activation and occlusive thrombus formation, thereby serving as first-in-class antiplatelet therapeutics with minimal risk of bleeding.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims.

What is claimed:

1. A compound of Formula (0), or a pharmaceutically acceptable salt thereof:

(0)

wherein:
A is —COOR$^1$, —OSO$_3$R$^1$, —OPO$_3$(R$^1$)$_2$, or -G-HET;
B is a bond each R$^1$ independently is H or C$_{1-6}$alkyl;
R$^2$ is H or OH;
each —is a single or double bond, provided that (i) when —at bond 2 is a single bond, then —at bond 1 is a trans double bond and R$^2$ is OH, and (ii) when —at bond 1 is a single bond, then —at bond 2 is a cis double bond and R$^2$ is H;
HET is an unsubstituted or substituted 5 to 10-membered heteroaryl group having 1, 2, 3, or 4 heteroatoms selected from the group consisting of N, S, or O;
G is O, S, NH, or absent;
C$_x$ is an alkylene group having x carbon atoms;
C$_y$ is an alkyl group having y carbon atoms;
x is 3, 4, 5, 6, or 7;
y is 4, 5, 6, 7;
and each carbon atom of the compound of Formula (0) independently is unsubstituted or substituted with one or more deuterium or fluorine atoms;

with the proviso that when x is 6, y is 5, and each carbon atom of Formula (I) is unsubstituted, then A is not —COOH.

2. The compound of claim 1, having a Formula (I) or (II):

(I)

(II)

3. The compound of claim 1, wherein A is —COOR$^1$, —OSO$_3$R$^1$, or —OPO$_3$(R$^1$)$_2$.
4. The compound of claim 1, wherein R$^1$ is H or CH$_3$.
5. The compound of claim 1, wherein A is -G-HET.
6. The compound of claim 5, wherein HET is a 5- or 6-membered heteroaryl group.
7. The compound of claim 6, wherein HET is tetrazolyl, triazolyl, or isoxazolyl.
8. The compound of claim 1, wherein G is absent.
9. The compound of claim 1, wherein G is O or S.
10. The compound of claim 1, wherein x is 4, 5, or 6; and/or y is 5.
11. The compound of claim 1, wherein at least one carbon atom is substituted with deuterium; and/or at least one carbon atom is substituted with fluorine.
12. The compound of claim 11, wherein the carbon atom at position 13 is disubstituted with deuterium or fluorine.
13. The compound of claim 1, wherein each carbon atom is mono- or disubstituted with either deuterium or fluorine.
14. The compound of claim 2, wherein the compound is of Formula 1 and has a structure selected from the group consisting of:

(Ia)

(Ib)

(Ic)

(Id)

-continued

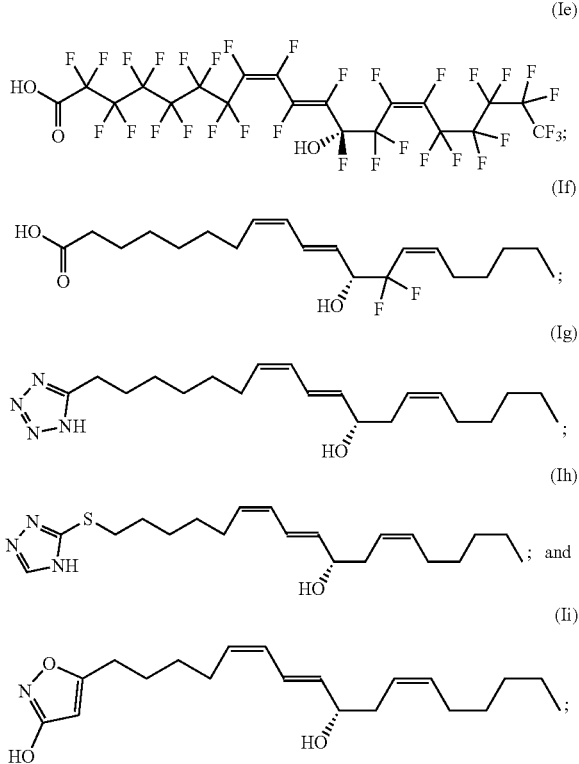

or wherein the compound is of Formula (II) and has a structure selected from the group consisting of:

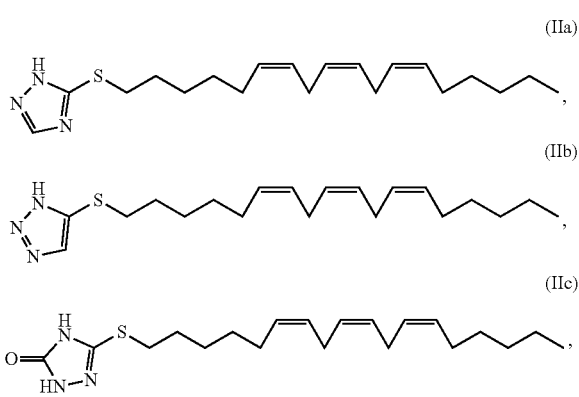

-continued

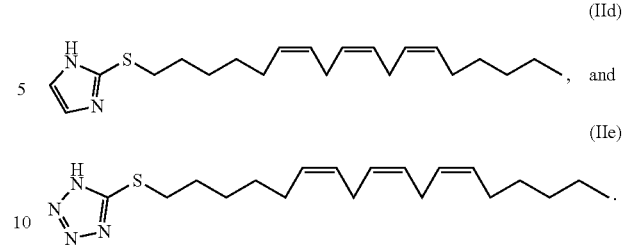

15. A composition comprising a therapeutically effective amount of a compound of claim 1 and a pharmaceutically acceptable carrier.

16. A method of treating a thrombotic disorder, preventing thrombosis, or treating thrombocytopenia in a subject having a thrombotic disorder thereof comprising administering a compound selected from 12(S)-hydroxy-8Z, 10E, 14Z-eicosatrienoic acid, a compound of claim 1, or a pharmaceutically acceptable salt of any of the foregoing to the subject in an amount effective to inhibit thrombus formation and/or loss of platelet cells while maintaining hemostasis.

17. The method of claim 16, wherein the subject has a thrombotic disorder selected from arterial thrombosis, deep vein thrombosis, pulmonary embolism, ischemic stroke, immune thrombocytopenia (ITP), Heparin-induced thrombocytopenia (HIT), and Heparin-induced thrombocytopenia and thrombosis (HITT).

18. The method of claim 16, comprising administering the compound to the subject before, during, and/or after a surgical procedure.

19. The method of claim 16, comprising administering the compound in an amount effective to:
   (i) inhibit platelet aggregation; or
   (ii) inhibit platelet integrin activation; or
   (iii) inhibit Rap1 activation; or
   (iv) activate G $\alpha_s$-linked G Protein-coupled receptors (GPCRs); or
   (v) activate cAMP; or
   (vi) activate protein kinase A (PKA); or
   (vii) inhibit thrombus growth; or
   (viii) combinations thereof.

20. The method of claim 16, comprising administering the compound to the subject at a dose between about 0.1 mg/kg and about 50 mg/kg and/or administering the compound orally or intravenously.

* * * * *